(12) United States Patent
Stephenson

(10) Patent No.: US 7,722,866 B2
(45) Date of Patent: May 25, 2010

(54) METHODS FOR REGULATING CANCER

(75) Inventor: Sally-Anne Stephenson, Hectorville (AU)

(73) Assignee: The Queen Elizabeth Hospital Research Foundation, Inc., Woodville (AU)

( * ) Notice: Subject to any disclaimer, the term of this patent is extended or adjusted under 35 U.S.C. 154(b) by 365 days.

(21) Appl. No.: 10/528,029

(22) PCT Filed: Sep. 16, 2003

(86) PCT No.: PCT/AU03/01209

§ 371 (c)(1),
(2), (4) Date: Dec. 16, 2005

(87) PCT Pub. No.: WO2004/024773

PCT Pub. Date: Mar. 25, 2004

(65) Prior Publication Data

US 2006/0134118 A1    Jun. 22, 2006

(30) Foreign Application Priority Data

Sep. 16, 2002    (AU) .............................. 2002951409

(51) Int. Cl.
*A61K 39/395* (2006.01)
(52) U.S. Cl. .................................. 424/130.1; 435/7.23
(58) Field of Classification Search ........................ None
See application file for complete search history.

(56) References Cited

U.S. PATENT DOCUMENTS 5,635,177 A * 6/1997 Bennett et al. ............ 424/143.1
2004/0180002 A1* 9/2004 Young et al. ................ 424/1.49
2005/0084873 A1    4/2005 Krasnoperov et al.

FOREIGN PATENT DOCUMENTS

WO    WO 02/26827 A1    4/2002
WO    WO 03/000113 A    1/2003

OTHER PUBLICATIONS

Noren et al, Cancer Res, 2007, 67:3994-3997.*
Gura, Science, 1997, 278:1041-1042.*
White et al, Annu Rev Med 52:125-145, 2001.*
Freshney, Culture of Animal Cells, A Manual of Basic Technique, Alan R. Liss, Inc., 1983, New York.*
Dermer, Bio/Technology, 1994, 12:320.*
Granziero et al., Eur. J. Immunol. 1999, 29:1127-1138.*
Byers, T.,CA Journal, vol. 49, No. 6, Nov./Dec. 1999.*
Lederman et al (Molecular Immunology 28:1171-1181, 1991.*
Li et al, Proc. Natl. Acad. Sci., 1980, 77:3211-3214.*
Bennett, B.D., et al., "Cloning and Characterization of *HTK*, a Novel Transmembrane Tyrosine Kinase of the *EPH* Subfamily," *J. Biol. Chem.* 269:14211-14218, American Society for Biochemistry and Molecular Biology, Inc. (1994).
Hall, S.M., et al., "Origin, Differentiation, and Maturation of Human Pulmonary Veins," *Am. J. Respir. Cell. Mol. Biol.* 26:333-340, American Thoracic Society (Mar. 2002).
Liu, W., et al., "Coexpression of Ephrin-Bs and their Receptors in Colon Carcinoma," *Cancer* 94:934-939, John Wiley & Sons, Inc. (Feb. 2002).
Stephenson. S.-A., et al., "Receptor protein tyrosine kinase EphB4 Is up-regulated in colon cancer," *BMC Mol. Biol.* 2:15, BioMed Central (Dec. 2001).
Takal, N., et al., "Expression of receptor tyrosine kinase EphB4 and its ligand ephrin-B2 is associated with malignant potential in endometrial cancer," *Oncol. Reports* 8:567-573, University of Crete, Faculty of Medicince, Laboratory of Clinical Virology (May 2001).
International Search Report for International Application No. PCT/AU03/01209, Australian Patent Office, Australia, mailed on Oct. 23, 2003.
Bodey, B. "Genetically engineered antibodies for direct antineoplastic treatment and systematic delivery of various therapeutic agents to cancer cells," Expert. Opin. Biol. Ther. 1:603-617 Ashley Publications Ltd (2001).
Cragg , M.S. et al., "Signaling antibodies in cancer therapy," *Cur. Opin. Immunol.* 11:541-547 Elsevier Science Ltd. (1999).
Hudson, P.J., "Recombinant antibody constructs in cancer therapy," *Cur. Opin. Immunol.* 11:548-557 Elsevier Science Ltd. (1999).
European Patent Office Examination Report dated Nov. 14, 2008, for corresponding application EP 03 794 710.8.

* cited by examiner

*Primary Examiner*—Misook Yu
*Assistant Examiner*—Mark Halvorson
(74) *Attorney, Agent, or Firm*—Sterne, Kessler, Goldstein & Fox P.L.L.C.

(57) ABSTRACT

The present invention provides methods for inhibiting cancerous growth of a cell using an antibody or an antigen-binding portion thereof which binds to an epitope of EphB4 polypeptide. Purified antibodies of EphB4 are also provided. The invention also provides methods for preventing or treating cancer. The invention also relates to methods of identifying agents that can inhibit cancerous growth of a cell.

17 Claims, 20 Drawing Sheets

Figure 11

201 TVNLTRFPETVPRELVVPVAGSCVVDAVPAPGPSPSLYCREDGQWAEQPVTGCS 254
TVNLTRFPETVPRELVVPVAGSCVV (SEQ ID NO:2- Peptide 1)
GSCVVDAVPAPGPSPSLYCREDGQW (SEQ ID NO:3- Peptide 2)
EDGQWAEQPVTGCS- 255 CAPGFEAAEGNTKCRACAQGTFKPLSGEGSCQPCPANSHSNTIGSAVCQCRVGY 308
CAPGFEAAEGN (SEQ ID NO:4- Peptide 3)
AAEGNTKCRACAQGTFKPLSGEGSC (SEQ ID NO:5- Peptide 4)
GEGSCQPCPANSHSNTIGSAVCQCR (SEQ ID NO: 6- Peptide 5)
VCQCRVGY- 309 FRARTDPRGAPCTTPPSAPRSVVSRLNGSSLHLEWSAPLESGGREDLTYALRCR 362
FRARTDPRGAPCTTPPS (SEQ ID NO:7- Peptide 6)

Figure 16

201    TVNLTRFPETVPRELVVPVAGSCVVDAVPAPGPSPSLYCREDGQWAEQPVTGCS    254
       TVNLTRFPETVPRELVVPVAGSCVV (SEQ ID NO:2- Peptide 1)

GSCVVDAVPAPGPSPSLYCREDGQW (SEQ ID NO:3- Peptide 2)

AGSCVVDA            (SEQ ID NO:8- Peptide 7)

VAGSCVVDAV           (SEQ ID NO:9-Peptide 8)

LVVPVAGSCVVDAVPA       (SEQ ID NO:10- Peptide 9)

Figure 18

SEQ ID NO:1

Homo Sapiens Ephrin type-B receptor 4 Precursor (EphB4)

| | | | | | | |
|---|---|---|---|---|---|---|
| 1 | MELRVLLCWA | SLAAALEETL | LNTKLETADL | KWVTFPQVDG | QWEELSGLDE | EQHSVRTYEV |
| 61 | CDVQRAPGQA | HWLRTGWVPR | RGAVHVYATL | RFTMLECLSL | PRAGRSCKET | FTVFYYESDA |
| 21 | DTATALTPAW | MENPYIKVDT | VAAEHLTRKR | PGAEATGKVN | VKTLRLGPLS | KAGFYLAFQD |
| 181 | QGACMALLSL | HLFYKKCAQL | TVNLTRFPET | VPRELVVPVA | GSCVVDAVPA | PGPSPSLYCR |
| 241 | EDGQWAEQPV | TGCSCAPGFE | AAEGNTKCRA | CAQGTFKPLS | GEGSCQPCPA | NSHSNTIGSA |
| 301 | VCQCRVGYFR | ARTDPRGAPC | TTPPSAPRSV | VSRLNGSSLH | LEWSAPLESG | GREDLTYALR |
| 361 | CRECRPGGSC | APCGGDLTFD | PGPRDLVEPW | VVVRGLRPDF | TYTFEVTALN | GVSSLATGPV |
| 421 | PFEPVNVTTD | REVPPAVSDI | RVTRSSPSSL | SLAWAVPRAP | SGAVLDYEVK | YHEKGAEGPS |
| 481 | SVRFLKTSEN | RAELRGLKRG | ASYLVQVRAR | SEAGYGPFGQ | EHHSQTQLDE | SEGWREQLAL |
| 541 | IAGTAVVGVV | LVLVVIVVAV | LCLRKQSNGR | EAEYSDKHGQ | YLIGHGTKVY | IDPFTYEDPN |
| 601 | EAVREFAKEI | DVSYVKIEEV | IGAGEFGEVC | RGRLKAPGKK | ESCVAIKTLK | GGYTERQRRE |
| 661 | FLSEASIMGQ | FEHPNIIRLE | GVVTNSMPVM | ILTEFMENGA | LDSFLRLNDG | QFTVIQLVGM |
| 721 | LRGIASGMRY | LAEMSYVHRD | LAARNILVNS | NLVCKVSDFG | LSRFLEENSS | DPTYTSSLGG |
| 781 | KIPIRWTAPE | AIAFRKFTSA | SDAWSYGIVM | WEVMSFGERP | YWDMSNQDVI | NAIEQDYRLP |
| 841 | PPPDCPTSLH | QLMLDCWQKD | RNARPRFPQV | VSALDKMIRN | PASLKIVARE | NGGASHPLLD |
| 901 | QRQPHYSAFG | SVGEWLRAIK | MGRYEESFAA | AGFGSFELVS | QISAEDLLRI | GVTLAGHQKK |
| 961 | ILASVQHMKS | QAKPGTPGGT | GGPAPQY | | | |

Figure 20
```
201 TVNLTRFPETVPRELVVPVAGSCVVDAVPAPGPSPSLYCREDGQWAEQPVTGCS 254
          AGSCVVDAVPAPGPSPSLYCREDGQ  (Peptide 11, SEQ IDNO:12)
                        |
          AGSCVVNAVPAPGPSPSLYCREDGQ  (Peptide 10, SEQ ID NO:11)
```
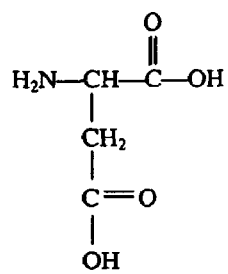
Aspartate (D)
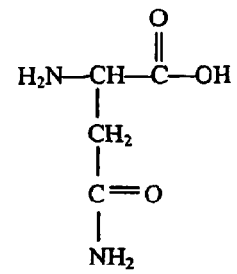
Asparagine (N)

METHODS FOR REGULATING CANCER

FIELD OF THE INVENTION

The present invention relates to methods for regulating cancer. In particular, the invention relates to methods for inhibiting cancerous growth of a cell. The invention also provides methods for preventing or treating cancer. The invention also relates to methods of identifying agents that can inhibit cancerous growth of a cell.

BACKGROUND OF THE INVENTION

Cancer describes a range of diseases, which result from dysregulated growth of cells of the body. Malignant cancers may develop from this dysregulated growth and subsequently spread around the body via the bloodstream or the lymphatic system, a process known as metastasis. Malignant tumours of epithelial tissues are the most common form of cancer and are responsible for the majority of cancer-related deaths in western industrialised countries. According to the Australian Institute of Health and Welfare (AIHW), on average one in three men and one in four women will develop cancer before the age of 75 years (1). In men the most common cancers are prostate, bowel and lung and in women, breast, bowel and melanoma. Identification of genes expressed specifically in tumour tissues and not in normal tissues, and analysis of their functions are useful for identifying new targets for cancer therapy.

Several genes have been implicated in various cancers. For instance, oncogenes are known to code for receptors for cellular growth factor such as epidermal growth factor. The ras gene is an oncogene that is believed to be responsible for up to 90% of all human pancreatic cancer, 50% of human colon cancers, 40% of lung cancers, and 30% of leukemias. Mutated oncogenes can become cancer-causing genes. Such mutated oncogenes code for proteins such as protein kinases and protein phosphorylating enzymes that trigger uncontrolled cell growth. EphB4 is a recently identified member of the largest known family of receptor protein tyrosine kinases. Eph receptor family members have been identified to be involved in many cellular processes including neural development, angiogenesis and vascular network assembly (2-5). As a result of interactions with their ligands, the ephrins, they mediate contact-dependent cell interactions, which regulate cell functions such as contact inhibition, cytoskeletal organisation and cell migration (6, 7).

Although a number of anti-cancer agents including growth inhibitory molecules such as cytoxic compounds have been developed in an attempt to treat cancer, there still remains a need for providing effective methods for regulating cancer.

SUMMARY OF THE INVENTION

The present invention is based on the surprising finding that an antibody that can bind to a particular region of the EphB4 protein can advantageously inhibit cancerous growth in a cancer cell by causing cell death of the cancer cell.

Therefore, in a first aspect the present invention provides a method for inhibiting cancerous growth of a cell, the method comprising contacting the cell with at least one antibody or an antigen-binding portion thereof, wherein the antibody or antigen-binding portion thereof binds to an epitope located within residues 200 to 400 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Preferably, the antibody or antigen-binding portion thereof binds to an epitope located within residues 220 to 244 of EphB4 (SEQ ID NO: 1), or a sequence at least 85%, preferably at least 90% identical thereto. Most preferably, the antibody or antigen-binding portion thereof binds to an epitope located within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

In a second aspect the present invention also provides a method for inducing cell death of a cancer cell, the method comprising contacting the cell with at least one antibody or an antigen-binding portion thereof, wherein the antibody or antigen-binding portion thereof binds to an epitope located within residues 200 to 400 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Preferably, the antibody or antigen-binding portion thereof binds to an epitope located within residues 220 to 244 of EphB4 (SEQ ID NO: 1), or a sequence at least 85%, preferably at least 90% identical thereto. Most preferably, the antibody or antigen-binding portion thereof binds to an epitope located within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

In a third aspect the present invention provides a method for treating or preventing cancer in a subject, the method comprising administering to the subject an effective amount of at least one antibody or an antigen-binding portion thereof, wherein the antibody or antigen-binding portion thereof binds to an epitope located within residues 200 to 400 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Preferably, the antibody or antigen-binding portion thereof binds to an epitope located within residues 220 to 244 of EphB4 (SEQ ID NO: 1), or a sequence at least 85%, preferably at least 90% identical thereto. Most preferably, the antibody or antigen-binding portion thereof binds to an epitope located within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

In another aspect of the invention there is provided a method of identifying an agent which inhibits cancerous growth of a cell, the method comprises assessing the ability of the agent to bind to an EphB4 polypeptide within the region of residues 200 to 400 of EphB4 (SEQ ID NO:1), or a sequence at least 85%, preferably at least 90% identical thereto. Preferably, the method comprises assessing the ability of the agent to bind to an EphB4 polypeptide within the region of residues 201 to 245 of EphB4 (SEQ ID NO: 1), or a sequence at least 85%, preferably at least 90% identical thereto. Preferably, the method comprises assessing the ability of the agent to bind to an EphB4 polypeptide within the region of residues 220 to 244 of EphB4 (SEQ ID) NO: 1), or a sequence at least 85%, preferably at least 90% identical thereto. Most preferably, the method comprises assessing the ability of the agent to bind to an EphB4 polypeptide within the region of residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

The present invention also provides an agent identified by the method described above.

In a further aspect of the invention there is provided a purified EphB4 antibody which binds to a polypeptide having a sequence at least 85% identical to residues 201 to 245 of EphB4 (SEQ ID NO: 1), preferably at least 90% identical to residues 201 to 245 of EphB4 (SEQ ID NO: 1). Preferably, the purified EphB4 antibody binds to a polypeptide having a sequence at least 85% identical to residues 220 to 244 of EphB4 (SEQ ID NO: 1), preferably at least 90% identical to residues 220 to 244 of EphB4 (SEQ ID NO: 1). The purified EphB4 antibody preferably binds to a polypeptide having a sequence at least 85% identical to residues 220 to 230 of EphB4 (SEQ ID NO: 1), preferably at least 90% identical to residues 220 to 230 of EphB4 (SEQ ID NO: 1). Most preferably, the present invention provides a purified EphB4 antibody which binds to an epitope located in residues 200 to 400 of EphB4 (SEQ ID NO: 1). The purified EphB4 antibody according to the present invention preferably binds to a polypeptide having a substitution of amino acid Asp (D) to Asn (N) at residue 226 of EphB4 (SEQ ID NO: 1). Preferably, the purified EphB4 antibody is a monoclonal antibody.

BRIEF DESCRIPTION OF THE FIGURES

FIG. 11 shows the sequences of the six overlapping peptides [shown as SEQ ID NO:2 (Peptide 1) to SEQ ID NO:7 (Peptide 6)] designed to span the first 125 amino acids of the target EphB4 sequence (shown in bold). The numbers refer to the position of the amino acids in the precursor EphB4 protein (SEQ ID NO:1 shown in FIG. 18).

FIG. 16 shows the sequences of the two overlapping peptides [shown as SEQ ID NO:2 (Peptide 1) and SEQ ID NO:3 (Peptide 2)] that were able to block the function of the EphB4 polyclonal antibody (H-200-Santa Cruz Biotechnology) specifically directed to the extracellular domain amino residues 201 to 400 of EphB4 (SEQ ID NO:1) on cells in culture and sequences of three peptides [shown as SEQ ID NO:8 (Peptide 7) to SEQ ID NO:10 (Peptide 9)] designed about the core sequence GSCVV for further narrowing of the reactive sequence. The numbers refer to the position of the amino acids in the precursor EphB4 protein (sequence shown in bold font).

FIG. 18 shows the amino acid sequence of SEQ ID NO:1. SEQ ID NO:1 is the amino acid sequence of precursor *Homo sapiens* Ephrin type-B receptor 4 (EphB4).

Figure 1:
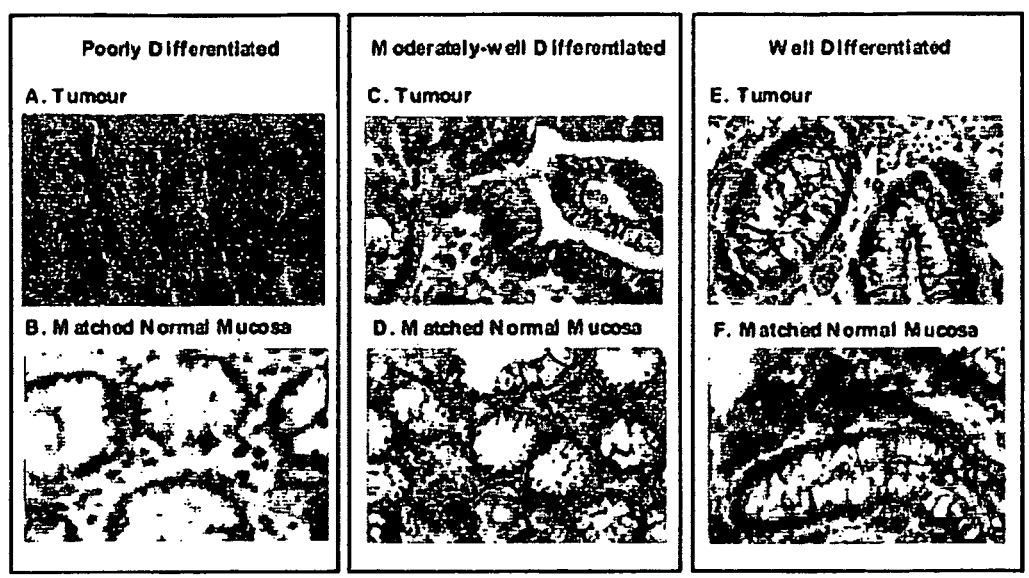
FIG. 1 shows immunohistochemical localisation of EphB4 expression in three different colon cancers and matched normal mucosa using the EphB4 polyclonal antibody (H-200-Santa Cruz Biotechnology) specifically directed to the extracellular domain amino residues 201 to 400 of EphB4 (SEQ ID NO:1). The dark stain from the biotinylated secondary antibody indicates the EphB4 protein. Nuclei are stained with Harris haematoxylin. High power (100×) magnification images of three different adenocarcinomas (well differentiated, moderately well differentiated and poorly differentiated) and their matched normal mucosa are shown. Strong staining of the tumour tissue and very weak, diffuse staining of normal tissue was evident for each sample set. There was no cross-reactivity with the secondary antibody alone (result not shown).

The placements of these domains relative to the EphB4 amino acid sequence is based on information taken from the most recent report from NCBI Accession number NP_004435. The N-19 Antibody maps to the N-terminal first 19 amino acids of the sequence which is likely to be amino acids residues 16 to 34 of the precursor EphB4 (SEQ ID NO:1). The C-16 antibody is directed to the tyrosine kinase domain. The H-200 antibody is specifically directed to residues 201 to 400 of EphB4 (SEQ ID NO:1) in the extracellular domain spanning the cysteine rich region and the fibronectin domain.

FIG. 20 shows a sequence of a Peptide 11 (SEQ ID NO:12) designed to include the proposed epitope sequence and a Peptide 10 (SEQ ID NO:11) in which the amino acid Aspartate (D) which carries a charge in this wild-type sequence is substituted with an uncharged amino acid with a similar side chain structure Asparagine (N). The numbers and the sequence in bold font refer to the position of the amino acids in the precursor EphB4 protein.

DETAILED DESCRIPTION OF THE INVENTION

In a first aspect the present invention provides a method for inhibiting cancerous growth of a cell, the method comprising contacting the cell with at least one antibody or an antigen-binding portion thereof, wherein the antibody or antigen-binding portion thereof binds to an epitope located within residues 200 to 400 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Most preferably, the antibody or antigen-binding portion thereof binds to an epitope located within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

The antibody or an antigen-binding portion thereof preferably specifically binds to a polypeptide having a sequence consisting of residues 200 to 400 of EphB4 (SEQ ID NO:1). Preferably, the antibody or antigen-binding portion specifically binds to a polypeptide having a sequence consisting of residues 201 to 245 of EphB4 (SEQ ID NO: 1), or a sequence at least 85%, preferably at least 90% identical thereto. Preferably, the antibody or antigen-binding portion specifically binds to a polypeptide having a sequence consisting of residues 220 to 244 of EphB4 (SEQ ID NO: 1), or a sequence at least 85%, preferably at least 90% identical thereto. Most preferably, the antibody or antigen-binding portion thereof specifically binds to a polypeptide having a sequence consisting of residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1). Most preferably, the antibody or an antigen-binding portion thereof is a polyclonal or monoclonal antibody. The method preferably results in the death of the cell.

The antibody or antigen-binding portion thereof preferably specifically binds to a polypeptide having a sequence at least 85%, preferably at least 90% identical to sequence selected from the group consisting of residues 200 to 400 of EphB4 (SEQ ID NO:1), residues 201 to 245 of EphB4 (SEQ ID NO: 1), residues 220 to 244 of EphB4 (SEQ ID NO: 1) and residues 220 to 230 of EphB4 (SEQ ID NO: 1). A polypeptide having a sequence at least 85%, preferably at least 90% identical to residues 200 to 400 of EphB4 (SEQ ID NO:1), residues 201 to 245 of EphB4 (SEQ ID NO: 1), residues 220 to 244 of EphB4 (SEQ ID NO: 1) or residues 220 to 230 of EphB4 (SEQ ID NO: 1), preferably includes polypeptide variants having at least one substitution, deletion or addition of particular amino acids(s). Such polypeptide variants are also suitable for the present methods, particularly if they retain antigenic properties. For instance, the polypeptide variants can be designed to retain antigenic properties and to improve polypeptide production and/or solubility.

For example, antigenic prediction programs suggest that the charged amino acid Asp (D) may also be important to the epitope function as it is the only charged residue in the sequence. Peptide 11 consisting of amino acid residues 220 to 244 of EphB4 protein (SEQ ID NO.1) was designed as indicated in FIG. 20. Peptide 10 with a substitution of Asn (N) at residue 226 of EphB4 protein (SEQ ID NO.1) was also designed as indicated in FIG. 20). The amino acid sequence of Peptide 10 and Peptide 11 is as follows:

```
Peptide 10 SEQ ID NO: 11:
AGSCVVNAVPAPGPSPSLYCREDGQ

Peptide 11 SEQ ID NO: 12:
AGSCVVDAVPAPGPSPSLYCREDGQ
```

The side chains of Asp and Asn are very similar—the hydoxyl group of Asp is an amine in Asn and changes it from being a negatively charged amino acid to a neutral one.

In a second aspect the present invention also provides a method for inducing cell death of a cancer cell, the method comprising contacting the cell with at least one antibody or an antigen-binding portion thereof, wherein the antibody or antigen-binding portion thereof binds to an epitope located within residues 200 to 400 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Preferably, the antibody or antigen-binding portion thereof binds to an epitope located within residues 220 to 244 of EphB4 (SEQ ID NO: 1), or a sequence at least 85%, preferably at least 90% identical thereto. Most preferably, the antibody or antigen-binding portion thereof binds to an epitope located within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

In a third aspect the present invention provides a method for treating or preventing cancer in a subject, the method comprising administering to the subject an effective amount of at least one antibody or an antigen-binding portion thereof, wherein the antibody or antigen-binding portion thereof binds to an epitope located within residues 200 to 400 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Most preferably, the antibody or antigen-binding portion thereof binds to an epitope located within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

The cancer is preferably selected from the group consisting of breast cancer, prostate cancer, bowel cancer, bladder cancer, colon cancer, ovarian cancer, lung cancer, melanoma, lymphoma and leukemia. The method preferably results in the death of a cancer cell in the subject.

In another aspect of the invention there is provided a method of identifying an agent which inhibits cancerous growth of a cell, the method comprising assessing the ability of the agent to bind to an EphB4 polypeptide within the region of 200 to 400 of EphB4 (SEQ ID NO:1), or a sequence at least 85%, preferably at least 90% identical thereto.

In a preferred embodiment of the invention, the agent binds to an epitope contained within residues 200 to 400 of EphB4 (SEQ ID NO:1), or a sequence at least 85%, preferably at least 90% identical thereto. Preferably, the agent binds to an epitope contained within residues 201 to 245 of EphB4 (SEQ ID NO: 1), or a sequence at least 85%, preferably at least 90% identical thereto. Preferably, the antibody or antigen-binding portion thereof binds to an epitope located within residues 201 to 245 of EphB4 (SEQ ID NO: 1), or a sequence at least 85%, preferably at least 90% identical thereto. Most preferably, the agent binds to an epitope contained within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

The present invention also provides an agent identified by the method described above.

In the present specification the term "antibody" is used in the broadest sense and specifically covers monoclonal antibodies, polyclonal antibodies, multispecific antibodies (e.g., bispecific antibodies), and antibody fragments. The term "epitope" refers to an epitope region of a polypeptide that is recognized by an antibody or an antigen binding portion thereof.

Antibodies refer to immunoglobulin molecules comprised of four polypeptide chains, two heavy (H) chains and two light (L) chains inter-connected by disulfide bonds. Each heavy chain is comprised of a heavy chain variable region (HCVR or VH) and a heavy chain constant region. The heavy chain constant region is comprised of three domains, CH1, CH2 and CH3. Each light chain is comprised of a light chain variable region (LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR, CDR1, FR2, CDR2, FR3, CDR3, FR4.

The term "antigen-binding portion" of an antibody (or simply "antibody portion"), as used herein refers to one or more fragments of an antibody that retains the ability to specifically bind to an antigen. It has been shown that the antigen-binding function of an antibody can be performed by fragments of a full length antibody. Examples of binding fragments encompassed within the term "antigen-binding portion" of an antibody include (I) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (8) which consists of a VH domain, or a VL domain (9); and (vi) an isolated complementarity determining region (CDR). Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv)(10), (11). Such single chain antibodies are also intended to be encompassed within the term "antigen-binding portion" of an antibody. Other forms of single chain antibodies, such as diabodies or triabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (12, 13). Preferably, the antibody is EphB4 (H-200) rabbit polyclonal Ig G antibody, Santa Cruz Biotechnology, Santa Cruz, Calif.

More preferably, the antibody is a monoclonal antibody or fragment thereof and, particularly, is selected from monoclonal antibodies or fragments thereof which bind to an epitope within residues 200 to 400 of EphB4 (SEQ ID NO:1), or a sequence at least 85%, preferably at least 90% identical thereto. Preferably, the monoclonal antibodies or fragments thereof bind to an epitope within residues 201 to 245 of EphB4 (SEQ ID NO: 1), or a sequence at least 85%, preferably at least 90% identical thereto. Preferably, the monoclonal antibodies or fragments thereof bind to an epitope within residues 220 to 244 of EphB4 (SEQ ID NO: 1), or a sequence at least 85%, preferably at least 90% identical thereto. Most preferably, the monoclonal antibodies or fragments thereof bind to an epitope within residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

In a further aspect of the invention there is provided a purified EphB4 antibody which binds to a polypeptide having a sequence at least 85% identical to residues 201 to 245 of EphB4 (SEQ ID NO: 1), preferably at least 90% identical to residues 201 to 245 of EphB4 (SEQ ID NO: 1). Preferably, the purified EphB4 antibody binds to a polypeptide having a sequence at least 85% identical to residues 220 to 244 of EphB4 (SEQ ID NO: 1), preferably at least 90% identical to residues 220 to 244 of EphB4 (SEQ ID NO: 1). The purified EphB4 antibody preferably binds to a polypeptide having a sequence at least 85% identical to residues 220 to 230 of EphB4 (SEQ ID NO: 1), preferably at least 90% identical to residues 220 to 230 of EphB4 (SEQ ID NO: 1). More preferably, the present invention provides a purified EphB4 antibody which binds to an epitope located in residues 200 to 400 of EphB4 (SEQ ID NO: 1). The purified EphB4 antibody according to the present invention preferably binds to a polypeptide having a substitution of amino acid Asp (D) to Asn (N) at residue 226 of EphB4 (SEQ ID NO: 1). More preferably, the purified EphB4 antibody is a monoclonal antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method, isolated from phage antibody libraries, or may be made by recombinant DNA methods. Such techniques include, but are not restricted to, the hybridoma technique (14), the trioma technique, the human B-cell hybridoma technique (15), and the EBV hybridoma technique to produce human monoclonal antibodies (16). In addition, humanised monoclonal antibodies can be generated according to methods described in U.S. Pat. No. 6,090,382 of which the entire description and references cited therein are incorporated herein. The document provides suitable host cells for expressing recombinant human antibodies and methods of synthesising the recombinant human antibodies. Furthermore, suitable human antibodies may be produced using transgenic animals using for example techniques described in Oncology 29 (Supp 4) 47-50 (2002). The antibodies of the present invention may also be obtained from commercial sources.

Various procedures known in the art may also be used for the production of polyclonal antibodies which can bind to a polypeptide having a sequence comprising residues 200 to 400 of EphB4 (SEQ ID NO:1), or a sequence at least 85%, preferably at least 90% identical thereto. For production of the antibodies, various host animals can be immunized by injection with a EphB4 protein or a EphB4 polypeptide fragment bound to a suitable carrier. Suitable carriers can include, but are not limited to, BSA (bovine serum albumin), KLH (keyhole limpet hemocyanin), OVA (ovalbumin), THY (Thyroglobulin) and RSA (rabbit serum albumin). The host animal is preferably immunized with a EphB4 polypeptide comprising residues 200 to 400 of EphB4 (SEQ ID NO:1), or a sequence at least 85%, preferably at least 90% identical thereto. Preferably, the host animals can be immunized by injection with a EphB4 protein or a polypeptide comprising residues 201 to 245 of EphB4 (SEQ ID NO: 1), or a sequence at least 85%, preferably at least 90% identical thereto. Preferably, the host animals can be immunized by injection with a EphB4 protein or a polypeptide comprising residues 220 to 244 of EphB4 (SEQ ID NO: 1), or a sequence at least 85%, preferably at least 90% identical thereto. Most preferably, the host animals can be immunized by injection with a EphB4 protein or a polypeptide comprising residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

Suitable host animals include, but are not limited to, rabbits, mice, rats, etc. Various adjuvants can be used to increase the immunological response, depending on the host species, and include, but are not limited to, Freud's (complete and incomplete), mineral gels such as aluminum hydroxide, surface active substances such as lysolecithin, pluronic polyols, polyanions, peptides, oil emulsions, dinitrophenol, and potentially useful human adjuvants such as *Badilus Calmette-Guerin* (BCG) and *Corynebacterium parvum*. Antibodies and antibody fragments may be produced in large amounts by standard techniques (eg in either tissue culture or serum free using a fermenter) and purified using affinity columns such as protein A (eg for murine Mabs), Protein G (eg for rat Mabs) or MEP HYPERCEL (eg for IgM and IgG Mabs).

Suitable antibodies may include antibody fragments that include an antigen-binding portion that can bind to a polypeptide having a sequence comprising residues 200 to 400 of EphB4 (SEQ ID NO:1), or a sequence at least 85%, preferably at least 90% identical thereto. The antigen-binding portion of an antibody preferably includes idiotypes of residues 200 to 400 of EphB4 (SEQ ID NO:1), or a sequence at least 85%, preferably at least 90% identical thereto. Preferably, the antibody fragments include an antigen-binding portion that can bind to a polypeptide having a sequence comprising residues 201 to 245 of EphB4 (SEQ ID NO: 1), or a sequence at least 85%, preferably at least 90% identical thereto. Preferably, the antibody fragments include an antigen-binding portion that can bind to a polypeptide having a sequence comprising residues 220 to 244 of EphB4 (SEQ ID NO: 1), or a sequence at least 85%, preferably at least 90% identical thereto. Most preferably, the antibody fragments include an antigen-binding portion that can bind to a polypeptide having a sequence comprising residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

Such antibody fragments can be generated by techniques known in the art. For example, such fragments include, but are not limited to, the F (ab')$_2$ fragment which can be produced by pepsin digestion of the antibody molecule; the Fab' fragments that can be generated by reducing the disulfide bridges of the F (ab')2 fragment, the Fab fragments that can be generated by treating the antibody molecule with papain and a reducing agent, and Fv fragments. In a further technique, recombinant antibodies specific to a polypeptide having a sequence comprising residues 200 to 400 of EphB4 (SEQ ID NO:1), preferably, residues 201 to 245 of EphB4 (SEQ ID NO:1), preferably, residues 220 to 244 of EphB4 (SEQ ID NO:1), more preferably, residues 220 to 230 of EphB4 (SEQ ID NO:1), or a sequence at least 85%, preferably at least 90% identical thereto, can be engineered and ectopically expressed in a wide variety of cell types. Preferably, the sequence has a substitution of amino acid Asp (D) to Asn (N) at residue 226 of EphB4 (SEQ ID NO: 1).

The antibodies used in the present methods can include "humanized" forms of non-human (eg., murine) antibodies that are immunoglobulins, immunoglobulin chains or fragments thereof (such as Fv, Fab, Fab', F(ab').sub.2 or other antigen-binding subsequences of antibodies) which contain minimal amino acid residues derived from a non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, a humanized antibody may comprise residues which are found neither in the recipient antibody nor in the imported CDR or framework sequences. These modifications can be made to further refine and optimize antibody performance.

The term "EphB4 protein" as used herein is taken to include full length EphB4 protein or a polypeptide fragment that comprises residues 200 to 400 of EphB4 (SEQ ID NO:1), or a sequence at least 85%, preferably at least 90% identical thereto. Preferably, the EphB4 protein includes a polypeptide fragment that comprises residues 201 to 245 of EphB4 (SEQ ID NO: 1), or a sequence at least 85%, preferably at least 90% identical thereto. Preferably, the EphB4 protein includes a polypeptide fragment that comprises residues 220 to 244 of EphB4 (SEQ ID NO: 1), or a sequence at least 85%, preferably at least 90% identical thereto. Most preferably, the EphB4 protein includes a polypeptide fragment that comprises residues 220 to 230 of EphB4 (SEQ ID NO: 1), or a sequence at least 85%, preferably at least 90% identical thereto. Preferably, the sequence has a substitution of amino acid Asp (D) to Asn (N) at residue 226 of EphB4 (SEQ ID NO: 1).

A EphB4 variant protein may been modified at the amino acid level and may include additions or deletions or replacements of amino acids which do not affect the functionality of the protein, such as conservative amino acid substitutions. An EphB4 protein may also include a truncated EphB4 protein. An EphB4 protein may be natural or recombinant. The EphB4 protein may be from any animal species, preferably the EphB4 protein is human.

An antibody or an antigen-binding portion thereof that is suitable for the methods of the present invention, preferably can inhibit cancerous growth of a cell by inhibiting the activity of an EphB4 protein. In the specification the term "cancerous growth" is taken to refer to abnormal and uncontrollable division and growth of a cell. Typically such a cell is identified as a cancer cell that may be able to invade and disrupt other tissues and has the potential to spread to other areas of the body. Cancerous growth of a cell can lead to the formation of a tumor that may be benign or malignant.

In the specification the term "cell(s)" is taken to include any cells. Preferably, the cells are derived from a mammalian species, such as, but not limited to, human, mice, bovine, sheep or domestic animals. It is preferred that the cells are selected from the group including, but not limited to, prostate cells, breast cells, colon cells, fibroblasts, epidermal cells, placental, liver, kidney, pancreas, heart, neural or muscle cells, or cancer or tumor cells. The cells may be normal cells, diseased cells, adult cells or embryonic cells. The cells may be single cells, cultured cells or part of a tissue. The cells may be genetically modified recombinant cells, such as a transgenic cell. Preferably, the cells express EphB4. The cells may be part of a whole animal. The cells may also be derived from a cell line. Preferably, the cells are from a cell line derived from, but not limited to, prostate, breast, colon or ovary cell line. The cell line is preferably selected from the group consisting of colon SW480, colon SW620, colon LIM1215, breast MCF7, breast T47-D, breast MDA-MB-231, breast MDA-MB-453, bladder J82, bladder T24, bladder RT119 and bladder 5637. More preferably, the cell line is selected from the group consisting of breast cancer cell line MCF-7 and colon cancer cell line SW480.

The antibody or an antigen-binding portion thereof of the present invention preferably can inhibit cancerous growth of one or more of cancer cells selected from the group consisting of breast cancer cells, prostate cancer cells, bowel cancer cells, bladder cancer cells, colon cancer cells, ovarian cancer cells, lung cancer cells, melanoma cells, lymphoma cells and leukemia cells.

The antibody or an antigen-binding portion thereof preferably specifically binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. In a preferred embodiment of the invention, at least one antibody or an antigen-binding portion thereof specifically binds to an epitope contained within residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto.

The term "specifically binds" in this specification, is to be understood to refer to binding characteristics of an antibody or an antigen-binding portion thereof which binds exclusively to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. The antibody or an antigen-binding portion thereof is preferably a polyclonal or monoclonal antibody that specifically binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Preferably, the antibody is an EphB4 polyclonal antibody (H-200-Santa Cruz Biotechnology) specifically directed to the extracellular domain amino residues 201 to 400 of EphB4 (SEQ ID NO:1).

The present invention provides a method for inhibiting cancerous growth of a cell, the method comprising contacting the cell with at least one antibody or an antigen-binding portion thereof, wherein the antibody or antigen-binding portion thereof binds to an epitope located within residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Preferably, the sequence has a substitution of amino acid Asp (D) to Asn (N) at residue 226 of EphB4 (SEQ ID NO: 1).

Preferably, at least one antibody or an antigen-binding portion thereof binds to a polypeptide having a sequence comprising residues 201 to 400 of EphB4 (SEQ ID NO:1), or a sequence at least 85%, preferably at least 90% identical thereto. Preferably, the antibody or an antigen-binding portion thereof binds to a EphB4 protein having a sequence comprising residues 201 to 245 of EphB4 (SEQ ID NO:1), or a sequence at least 85%, preferably at least 90% identical thereto. Preferably, the antibody or an antigen-binding portion thereof binds to a EphB4 protein having a sequence comprising residues 220 to 244 of EphB4 (SEQ ID NO:1), or a sequence at least 85%, preferably at least 90% identical thereto. More preferably, the antibody or an antigen-binding portion thereof binds to a EphB4 protein having a sequence comprising residues 220 to 230 of EphB4 (SEQ ID NO:1), or a sequence at least 85%, preferably at least 90% identical thereto. Preferably, the sequence has a substitution of amino acid Asp (D) to Asn (N) at residue 226 of EphB4 (SEQ ID NO: 1).

The phrase "inhibiting cancerous growth of a cell" as used herein is taken to mean that cancerous growth of the cell is substantially reduced or prevented. In the present invention a cell is contacted with at least one antibody or an antigen-binding portion thereof which binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto, to result in the inhibition of cancerous growth of the cell as compared to an untreated cell. The method preferably results in the death of the cell. Preferably, the sequence has a substitution of amino acid Asp (D) to Asn (N) at residue 226 of EphB4 (SEQ ID NO: 1).

The present invention also provides a method for inducing cell death of a cancer cell, the method comprising contacting the cell with at least one antibody or an antigen-binding portion thereof which binds to a polypeptide having a sequence comprising residues 200 to 400 of EphB4 (SEQ ID NO:1), or a sequence at least 85%, preferably at least 90% identical thereto. In a preferred embodiment of the invention, at least one antibody or an antigen-binding portion thereof binds to an epitope contained within residues 201 to 245 of EphB4 (SEQ ID NO:1), or a sequence at least 85%, preferably at least 90% identical thereto. Preferably, at least one antibody or an antigen-binding portion thereof binds to an epitope contained within residues 220 to 244 of EphB4 (SEQ ID NO:1), or a sequence at least 85%, preferably at least 90% identical thereto. More preferably, at least one antibody or an antigen-binding portion thereof binds to an epitope contained within residues 220 to 230 of EphB4 (SEQ ID NO:1), or a sequence at least 85%, preferably at least 90% identical thereto. Preferably, the sequence has a substitution of amino acid Asp (D) to Asn (N) at residue 226 of EphB4 (SEQ ID NO: 1).

The phrase "inducing cell death of a cancer cell" is taken to mean that a cancer cell contacted with at least one antibody or an antigen-binding portion thereof which binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto, is caused to undergo cell death. Preferably, the antibody is an EphB4 polyclonal antibody (H-200-Santa Cruz Biotechnology) specifically directed to the extracellular domain amino residues 201 to 400 of EphB4 (SEQ ID NO:1).

Cell death of a cancer cell may be assessed by a number of assays. For example, caspase-3 activation is considered to play a key role in the initiation of cellular events during cell death. Many different kits for the quantification of caspase-3 activity are available commercially. Mitochondrial membrane depolarization is often associated with the early stage of cell death. Changes in the membrane potential are presumed to be due to the opening of the mitochondrial permeability transition pores, which may play a central role in apoptosis. Depolarization can be detected by a number of different assays including the use of Rhodamine 123, a green-fluorescent cationic dye that accumulates in active mitochondria, which have high membrane potentials allowing quick and easy detection o cellular disruption. Lactate dehydrogenase (LDH) is a stable cytoplasmic enzyme present in all cells. It is rapidly released into the cell culture supernatant when the plasma membrane is damaged. LDH activity can easily be measured in culture supernatant by a single point assay using a spectrophotometric plate reader using commercially available kits. Elevated LDH in the culture medium is an indication of cell necrosis (death).

The morphology of a cell can also be examined to assess cell death. For instance, apoptosis is programmed cell death which is characterised by a series of typical morphological events, such as shrinkage of the cell and fragmentation into membrane-bound apoptotic bodies (17). These can be seen using a light microscope. In addition, a cell can be examined for the expression of genes related to cell death. In addition, RT-PCR analysis comparing EphB4 antibody treated and untreated cells from four different breast cancer cell lines has shown that EphB4 gene expression is down-regulated in treated cells.

A further aspect of the present invention is a method for treating or preventing cancer in a subject, the method comprising administering to the subject an effective amount of at least one antibody or an antigen-binding portion thereof which binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Preferably, the sequence has a substitution of amino acid Asp (D) to Asn (N) at residue 226 of EphB4 (SEQ ID NO: 1). The method preferably results in the death of a cancer cell in the subject.

The cancer is preferably selected from the group consisting of breast cancer, prostate cancer, bowel cancer, bladder cancer, colon cancer, ovarian cancer, lung cancer, melanoma, lymphoma and leukemia.

The subject treated by the methods of the invention may be selected from, but is not limited to, the group consisting of humans, sheep, cattle, horses, bovine, pigs, poultry, dogs and cats.

In the method an effective amount of at least one antibody or an antigen-binding portion thereof which binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto, is administered to a subject. In a preferred embodiment of the invention, at least one antibody or an antigen-binding portion thereof binds to an epitope contained within residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. The antibody or an antigen-binding portion thereof preferably specifically binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Most preferably, the antibody or an antigen-binding portion thereof is a polyclonal or monoclonal antibody.

The term "effective amount" means a dosage sufficient to provide treatment or prevention for the cancer being treated or prevented. This will vary depending on the subject and the type of cancer being effected. The effective amounts of at least one antibody or an antigen-binding portion thereof used in the methods of the present invention may vary depending upon the manner of administration, the condition of the animal to be treated, and ultimately will be decided by the attending scientist, physician or veterinarian. The amount of antibody or an antigen-binding portion thereof used to treat or prevent a subject will also vary depending upon the nature and identity of the particular antibody or an antigen-binding portion thereof.

An antibody or an antigen-binding portion thereof is preferably administered to a subject by any suitable means known to those skilled in the art. Preferably, the antibody or an antigen-binding portion thereof can be contacted with a cell in numerous fashions, including, for example, intravenously.

Preferably, the antibody or an antigen-binding portion thereof of the present invention is combined with a suitable pharmaceutically-acceptable carrier or diluent to form a pharmaceutical composition which may be suitable for administration to a human or animal subject. Suitable carriers or diluents include isotonic saline solutions, for example, phosphate-buffered saline. The pharmaceutical composition including at least one antibody or an antigen-binding portion thereof may be formulated for parenteral, intramuscular, intravenous, subcutaneous, intraocular, oral or transdermal administration. The antibody may be administered at a suitable dose dependent on the body weight of the subject. It is to be understood, however, that the routes of administration and dosages mentioned are intended to serve only as a guide since a person skilled in the art would be able to readily determine the optimum route of administration and dosage for any particular subject and cancer.

The antibody or an antigen-binding portion thereof used in the methods of the present invention may be combined with suitable excipients, such as emulsifiers, surfactants, stabilisers, dyes, penetration enhancers, anti-oxidants, water, salt solutions, alcohols, polyethylene glycols, gelatine, lactose, magnesium sterate and silicic acid. The antibody or an antigen-binding portion thereof is preferably formulated as a sterile aqueous solution. The antibody or an antigen-binding portion thereof can be combined with adjunct components that are compatible with the activity of the antibody. An antibody or an antigen-binding portion thereof used in the methods of the present invention may be preferably used to complement existing treatments for cancer. For example, the method of the present invention may also be used in combination with traditional cancer treatments such as radiotherapy, chemotherapy (eg using anthracyclines, 5FU, topoisomerase inhibitors, Cisplatin and Carboplatin), or hormone therapy or therapies utilising hormone modifiers (eg Catamoxifen).

In another aspect of the invention there is provided a method of identifying an agent which inhibits cancerous growth of a cell, the method comprising assessing the ability of the agent to bind to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. In a preferred embodiment of the invention, the agent binds to an epitope contained within residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Preferably, the agent binds to a EphB4 protein having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto.

In the present specification the term "agent" is taken to include any molecule, compound or protein that can bind (interact with) residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Suitable agents can preferably include an antibody or an antigen-binding portion thereof that binds to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Most preferably, the agent is an antibody or an antigen-binding portion thereof that is a polyclonal or monoclonal antibody. The method preferably comprises assessing the ability of the agent to induce cell death of a cancer cell. The agent is preferably a EphB4 ligand, such as an antibody or an antigen-binding portion thereof, that is preferably specific for EphB4 protein and may be developed or obtained commercially for testing in in vitro or in vivo systems for its ability to inhibit cancerous growth of a cell.

For instance, antibodies or antigen-binding portions thereof directed to specific epitopes of residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto, can be tested for their ability to inhibit cancerous growth of a cell and preferably induce cell death. Dose response curves to assess the IC50 of the antibodies can be conducted to test efficacy of each antibody tested. In addition, antibody/receptor-ligand binding studies can be performed to assess the ability of the antibody to prevent ligand binding. Tyrosine phosphorylation of the EphB4 receptor following antibody binding can be assessed by immunoprecipitation of the receptor with the respective antibody, followed by Western analysis with an anti-phosphotyrosine antibody to confirm that the EphB4 receptor is inactivated. The antibody with the best neutralising activity in terms of inhibiting tyrosine phosphorylation and cell growth in vitro and preventing ligand binding to the EphB4 receptor at the lowest 50% inhibitory concentration ($IC_{50}$) can be selected for additional in vivo tests.

For instance, an in vivo model of metastasis and tumour growth using immune-deficient NOD-SCID (non-obese diabetic, combined immunodeficiency) mice can be used to test the ability of putative agents that can bind to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto, for their efficacy as an anti-cancer agent. Preferably, the sequence has a substitution of amino acid Asp (D) to Asn (N) at residue 226 of EphB4 (SEQ ID NO: 1). Moreover, a diverse array of tumor cell lines that are available, most of which can be grown as xenografts, and these include the human breast cancer cell line MCF-7 and colon cancer cell line HT29, can be used for in vitro testing. Xenograft tumours can be grown in the mouse model either after subcutaneous injection, where they will grow as a mass, or after injection into the tail vein allowing mimicry of the hematogenous spread of metastasis that results in secondary deposits in other organs. Once suitable engraftment periods and inoculation doses for each cell line have been established, the model can be used to test various agents that bind to a polypeptide having a sequence comprising residues 200 to 400 of EphB4 (SEQ ID NO:1), preferably residues 201 to 245 of EphB4 (SEQ ID NO:1), preferably residues 220 to 244 of EphB4 (SEQ ID NO:1), more preferably residues 220 to 230 of EphB4 (SEQ ID NO:1), or a sequence at least 85%, preferably at least 90% identical thereto. Cells may also be treated with sub-lethal doses of a chosen EphB4 antibody equating to the $IC_{50}$ and $IC_{75}$ to assess the engraftment of treated cells compared with non-treated cells. This will assess the effects of reduced functional expression of EphB4 on establishment and metastasis of tumour cell lines.

The in vivo models can also be used for pre-clinical assessment of potential new therapies for treatment of EphB4 positive tumours cell lines. The use of subcutaneous injection will allow the examination of tumours that have been allowed to establish for different periods of time. This can be used to determine the ability of an agent, such as an antibody or an antigen-binding portion thereof, to ablate newly and well-established tumours compared to vehicle control. The use of tail vein injections can be used to determine whether treatment with an antibody or an antigen-binding portion thereof will reduce number of metastases formed as a result of hematogenous spread. The agents identified by the methods of the present invention may be used for treatment or prevention of cancer. The present invention also provides an agent identified by the method described above.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

EXAMPLE 1

Immunohistochemical Localisation of EphB4

An EphB4 polyclonal antibody (H-200-Santa Cruz Biotechnology) specifically directed to the extracellular domain amino residues 201 to 400 of EphB4 (SEQ ID NO:1) was used to analyse the localisation of the EphB4 protein in tumour and normal tissue. Colon and breast tissue showed marked increase in the levels of this protein in the tumour epithelial cells when compared with the matched normal tissue (as shown in FIG. 1). The demonstration of high expression of EphB4 on the tumour epithelial cells in two of the most commonly occurring cancers suggests that EphB4 is critical to the progression of these tumours.

EXAMPLE 2

RT-PCR Expression of EphB4

Figure 2:
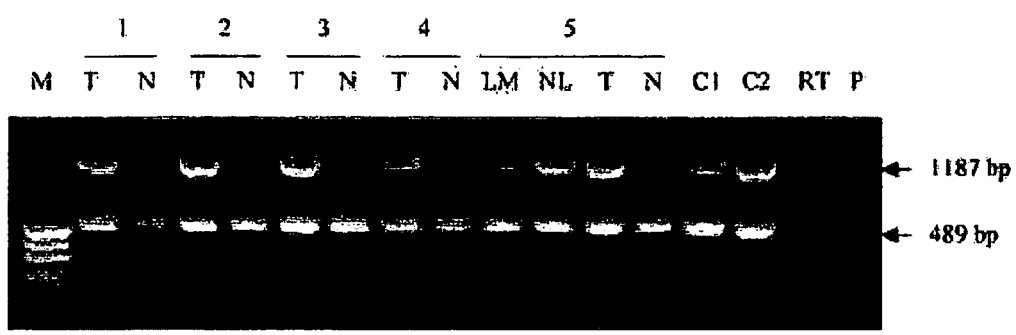
FIG. 2 shows relative RT-PCR comparing expression of EphB4(1187 bp) and internal 18S rRNA (489 bp) in five tumour (T)/normal (N) pairs. LM—Liver metastasis and NL—normal liver from patients 5, C1—colon cancer cell line LIM2405, C2—colon cancer cell line SW480, RT—RT negative control, P—PCR negative control, M—pUC19/HpaII marker.

Reverse transcriptase-polymerase chain reaction (RT-PCR) was used to compare expression of EphB4(1187 bp) and internal 18S rRNA (489 bp) in five tumour (T)/normal (N) pairs (results shown in FIG. 2). Analysis of 63 colon cancers from 60 patients indicated that EphB4 is over-expressed in the tumour tissue of 80% of patients, implying broad application as a therapeutic target (FIG. 2). The differential expression between tumour cells and normal tissue suggests anti-EphB4 tumour therapy may have a preferential effect on colon (and other) tumours.

A comparison of the expression profile of EphB4 with that of other receptor protein tyrosine kinases already being targeted in clinical trials (HER2, EGFR and VEGFR) suggests that EphB4 is expressed to a lesser degree in normal tissues. Information from EST databases suggests that low level expression of EphB4 may be present in kidney, ovary and placenta, and very low level expression in heart, lung, peripheral nerves and vascular tissue. Accordingly therapies that target EphB4 may be expected to produce less side effects than those that target other receptor tyrosine kinases.

EXAMPLE 3

EphB4-Specific Antibody Studies

Figure 3:
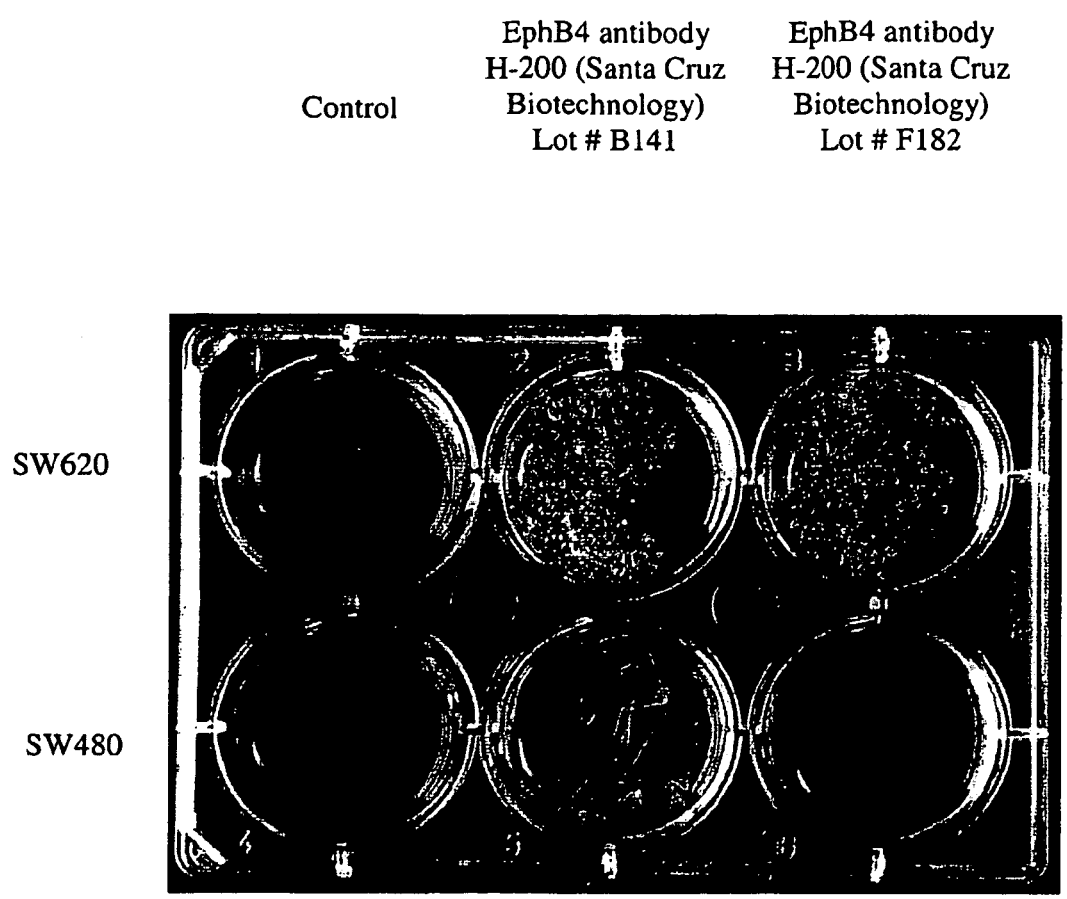
FIG. 3 shows a confluent monolayer of cells in 2 ml DMEM is treated with a 1/500 dilution of the EphB4 polyclonal antibody (H-200-Santa Cruz Biotechnology) specifically directed to the extracellular domain amino residues 201 to 400 of EphB4 (SEQ ID NO:1) (0.4 ng/μl final concentration). Incubation of cells with the antibody causes a visual response between 24 and 48 h. The cells lift off the bottom of the culture vessel in a fragile sheet which breaks up easily on gentle agitation. The change in colour of the media is due to a 0.5 pH unit change attributed to the leakage of cellular contents from dead cells.

A direct tumoricidal effect of an EphB4 polyclonal antibody (H-200-Santa Cruz Biotechnology) specifically directed to the extracellular domain amino residues 201 to 400 of EphB4 (SEQ ID NO:1) in vitro was demonstrated. Incubation of a fully confluent monolayer of colon cancer cell lines SW480 and SW620 with a 1/500 dilution of EphB4 antibody H-200 (Santa Cruz Biotechnology—Lot numbers B141 and F182) caused the cells to lift of the bottom of the culture vessel and die (FIG. 3). This was a common response seen when treating colon cancer cell lines including SW480, SW620, LIM1215, breast cancer cell lines MCF-7, T47-D, MDA-MB-453, MDA-MB-231 and Hs578t, bladder cancer cell lines J82, RT119, 5637 and T24.

Figure 4:
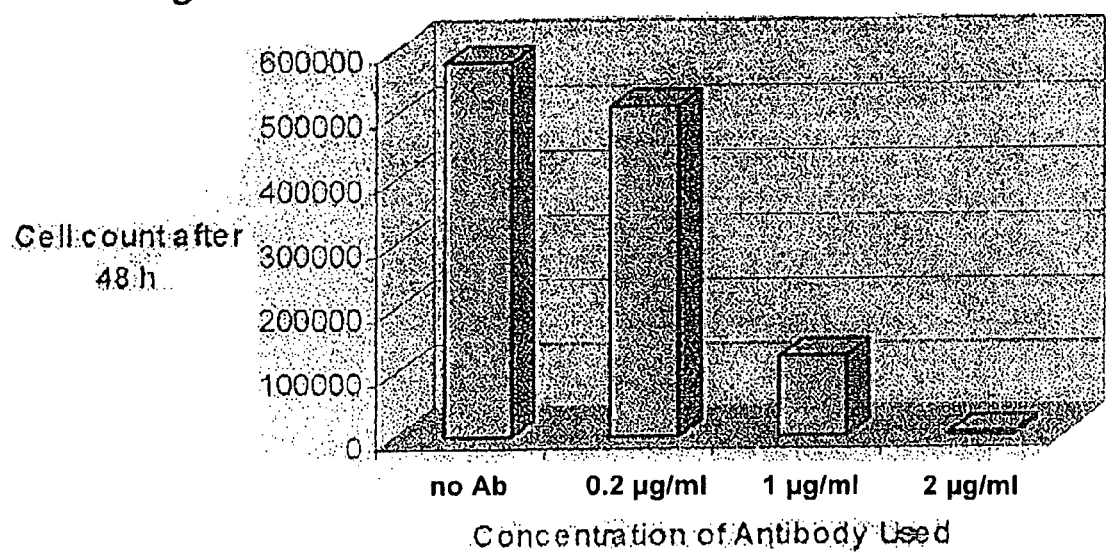
FIG. 4 shows a graph showing effect of increased doses of an EphB4 polyclonal antibody (H-200-Santa Cruz Biotechnology) specifically directed to the extracellular domain amino residues 201 to 400 of EphB4 (SEQ ID NO:1) on growth of MCF-7 cells in vitro after 48 hours.
Figure 5:
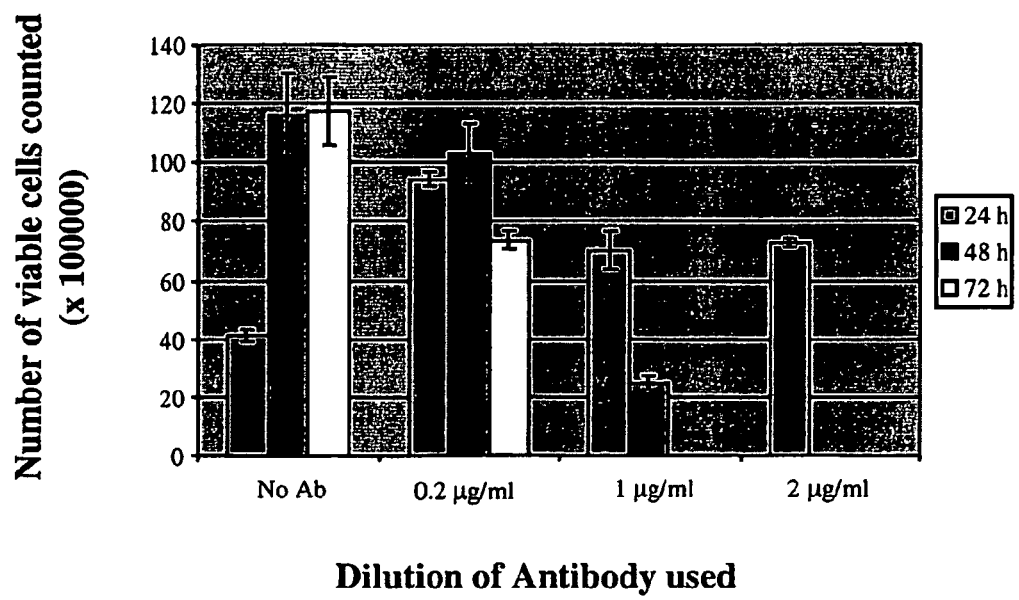
FIG. 5 shows a trypan blue exclusion assay to determine dose dependency of an EphB4 polyclonal antibody (H-200-Santa Cruz Biotechnology) specifically directed to the extracellular domain amino residues 201 to 400 of EphB4 (SEQ ID NO:1). The number of viable cells (x100000) (Y-axis) decreases after 48 h exposure to three different dilutions of the EphB4 antibody (X-axis). There were no viable cells remaining after 72 h with the addition of 1 μg/ml and after 48 h with the addition of 2 μg/ml.
Figure 6:
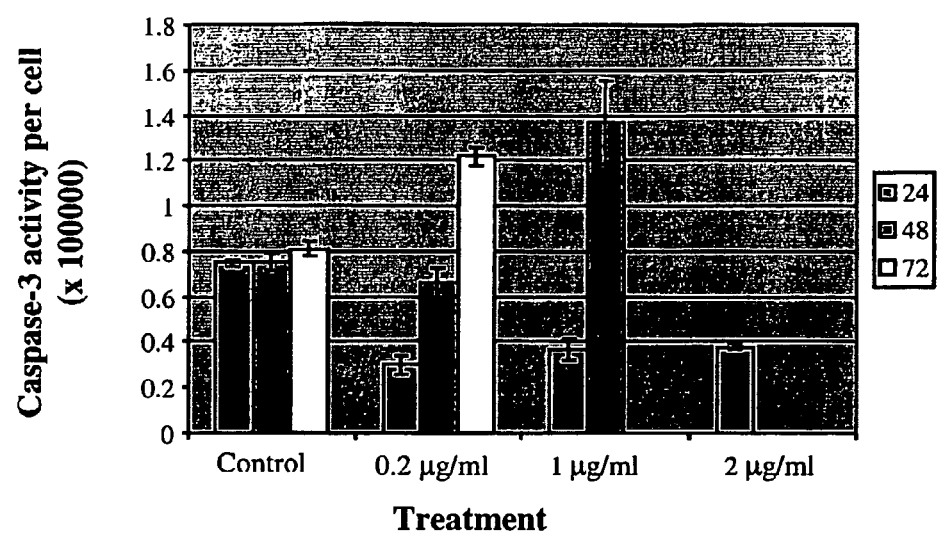
FIG. 6 shows a Caspase-3 assay. The relative amount of caspase-3 activity per 100000 cells (Y-axis) increases after time for all dilutions of an EphB4 polyclonal antibody (H-200-Santa Cruz Biotechnology) specifically directed to the extracellular domain amino residues 201 to 400 of EphB4 (SEQ ID NO:1) (X-axis). Because there were no viable cells counted for 1/200 dilution (1 μg/ml) after 72 h and for the 1/100 (2 μg/ml) dilution after 48 h, caspase-3 activity was not measured.

Incubation of the breast cancer cell line MCF-7 and the colon cancer cell line SW480 with three different concentrations of antibody (2 µg/ml, 1 µg/µml and 0.2 µg/ml) resulted in cell death in a dose dependent manner (see FIG. 4 and FIG. 5). This effect was not seen following exposure of the endothelial cell line HUVEC-C to the EphB4 antibody. Analysis of the caspase-3 activity suggested that cell death was not via apoptosis (FIG. 6). These results suggest that by cross-linking or binding to membrane receptors, antibodies may mimic or modulate receptor activity and that these antibodies-generated transmembrane signals might cause apoptosis or growth inhibition (18). Possible alternative mechanisms for the induction of cell death include ras-mediated non-apoptotic cell death or restoration of gap junction intercellular communication (GJIC), a direct cell-cell communication pathway that is known to be prevented by Eph receptor signaling (19).

Figure 7:
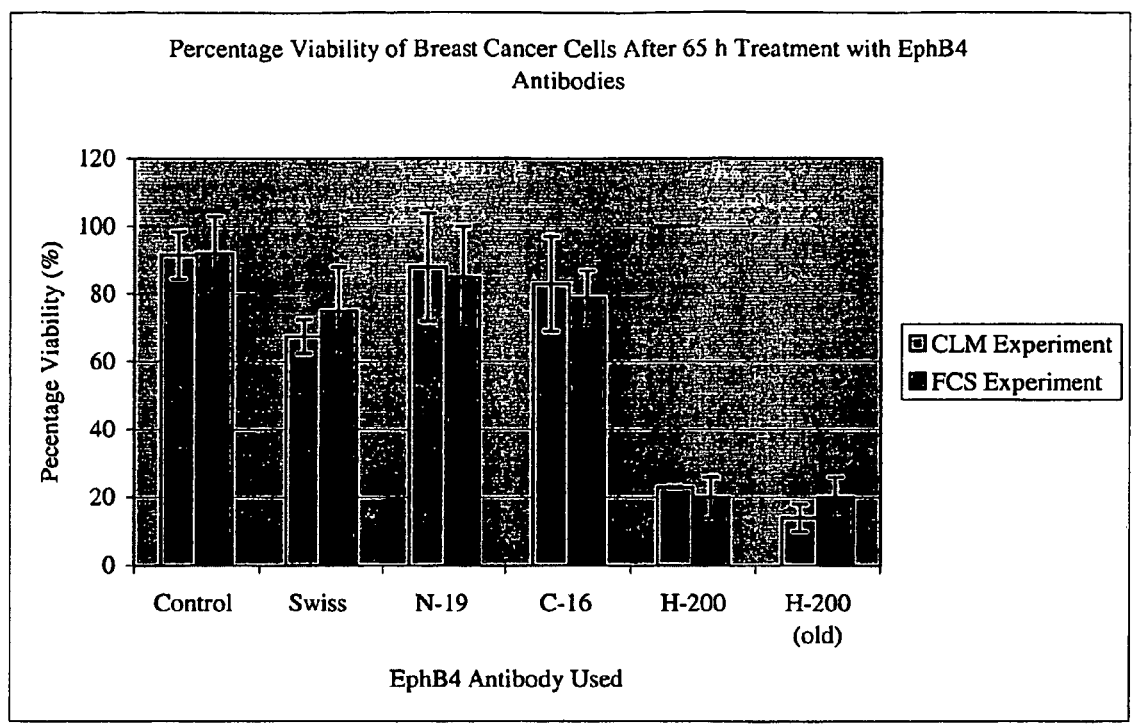
FIG. 7 shows a graph showing percentage viability of breast cancer cells after 65 h treatment with five different EphB4 antibodies: (1) a EphB4 polyclonal antibody (Swiss) directed to amino acid residues 825 to 991 of the carboxy terminus of mouse EphB4 (gift from Dr Andrew Ziemiecki, University of Bern), (2) a polyclonal N-terminal EphB4 antibody (N-19 Santa Cruz Biotechnology) directed to the N-terminal first 19 amino acids of the EphB4 amino acid sequence which is likely to be amino acids residues 16 to 34 of the precursor EphB4 (SEQ ID NO:1), (3) a polyclonal EphB4 C-terminal antibody (C-16 Santa Cruz Biotechnology) directed to the carboxy-terminal corresponding to tyrosine kinase domain consisting of amino acid residues 615 to 874 of EphB4 (SEQ ID NO:1), (4) a EphB4 polyclonal antibody (H-200-Santa Cruz Biotechnology) specifically directed to the extracellular domain amino residues 201 to 400 of EphB4 (SEQ ID NO:1) and (5) EphB4 polyclonal antibody (H-200 (old)-Santa Cruz Biotechnology-Lot number B141 batch) specifically directed to the extracellular domain amino residues 201 to 400 of EphB4 (SEQ ID NO:1). Cells were treated with 1/100 dilution of stock antibody (200 μg/ml), then stained with trypan blue (stains dead cells). Ratios of unstained (viable) to stained (unviable) were calculated for four different aliquots of each treatment. Control—no antibody added. CLM—complement limited medium. FCS—10% Fetal calf serum added to medium. Complement does not play a role in the cell death effect of the EphB4 polyclonal antibody (H-200-Santa Cruz Biotechnology) specifically directed to the extracellular domain amino residues 201 to 400 of EphB4 (SEQ ID NO:1). This is demonstrated by the comparison of percentage viability after antibody addition to cells grown in medium with normal protein activity (FCS experiment) with cells grown in medium in which complement proteins were inactivated by heating to 55° C. for 30 mins (CLM Experiment).

Polyclonal antibodies specific for EphB4 have been developed and are available commercially, for testing of these antibodies in vitro and in vivo systems. FIG. 7 shows results of the percentage viability of breast cancer cells after treatment with five EphB4 antibodies as detailed below:

(1) a EphB4 polyclonal antibody (Swiss) directed to amino acid residues 825 to 991 of the carboxy terminus of mouse EphB4;
(2) a polyclonal N-terminal EphB4 antibody (N-19 Santa Cruz Biotechnology) directed to the N-terminal first 19 amino acids of the EphB4 amino acid sequence which is likely to be amino acids residues 16 to 34 of the precursor EphB4 (SEQ ID NO:1);
(3) a polyclonal EphB4 C-terminal antibody (C-16 Santa Cruz Biotechnology) directed to the carboxy-terminal corresponding to tyrosine kinase domain consisting of amino acid residues 615 to 874 of EphB4 (SEQ ID NO:1);
(4) a EphB4 polyclonal antibody (H-200-Santa Cruz Biotechnology) specifically directed to the extracellular domain amino residues 201 to 400 of EphB4 (SEQ ID NO:1);
(5) a EphB4 polyclonal antibody (H-200 (old)-Santa Cruz Biotechnology-Lot number B141 batch) specifically directed to the extracellular domain amino residues 201 to 400 of EphB4 (SEQ ID NO:1).

Cell death effect was seen in treatment with the H-200 antibody specifically directed to the extracellular domain amino residues 201 to 400 of EphB4 (SEQ ID NO:1). A comparison of cells grown in medium with or without active complement proteins shows that complement plays no role in the Ab-mediated cell death (see FIG. 7).

The mechanism of cell death can be further by analysing changes to gene expression induced in cancer cells in vitro after incubation with sub-lethal doses of the H-200 EphB4 antibody using microarray techniques.

EXAMPLE 4

Expression of EphB4 in Human Tissue

Figure 8:
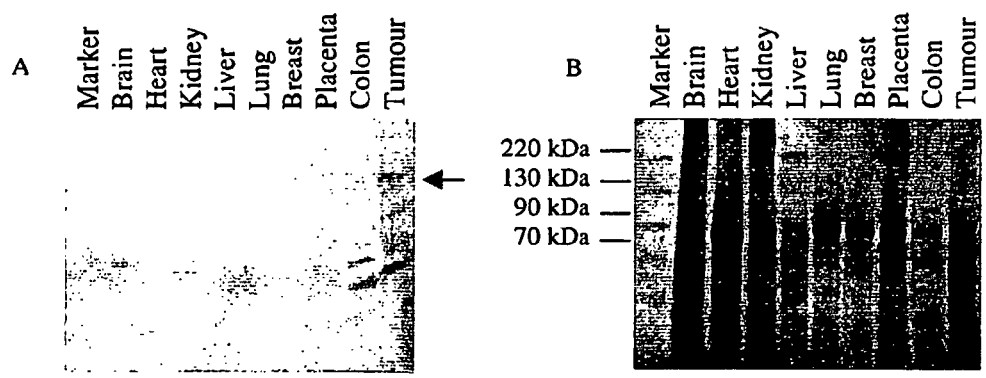
FIG. 8 shows a western analysis of normal human tissues as indicated and a representative colon tumour (Tumour). (A) EphB4 protein was identified using a EphB4 polyclonal antibody (H-200-Santa Cruz Biotechnology) specifically directed to the extracellular domain amino residues 201 to 400 of EphB4 (SEQ ID NO:1). Predicted wildtype protein is 120 kDa and is indicated by the arrow. (B) Coomassie blue stained duplicate gel. Sizes of molecular weight marker are as indicated.

Information from EST databases and Northern analysis of normal human tissues (20) suggests that low level expression of EphB4 may be present in kidney, ovary and placenta, and very low level expression in heart, lung, peripheral nerves and vascular tissue, and no expression in brain. In order to determine whether gene expression correlates with the level of protein actually translated a western analysis using these tissues was performed with an EphB4 polyclonal antibody (H-200-Santa Cruz Biotechnology) specifically directed to the extracellular domain amino residues 201 to 400 of EphB4 (SEQ ID NO:1). By comparison with a single colon tumour sample it was shown that the level of gene expression does not correspond to the amount of EphB4 protein produced in these tissues (FIG. 8). The differential expression between tumour cells and normal tissue suggests that anti-EphB4 tumour therapy may have a preferential effect on colon tumours.

Figure 9:
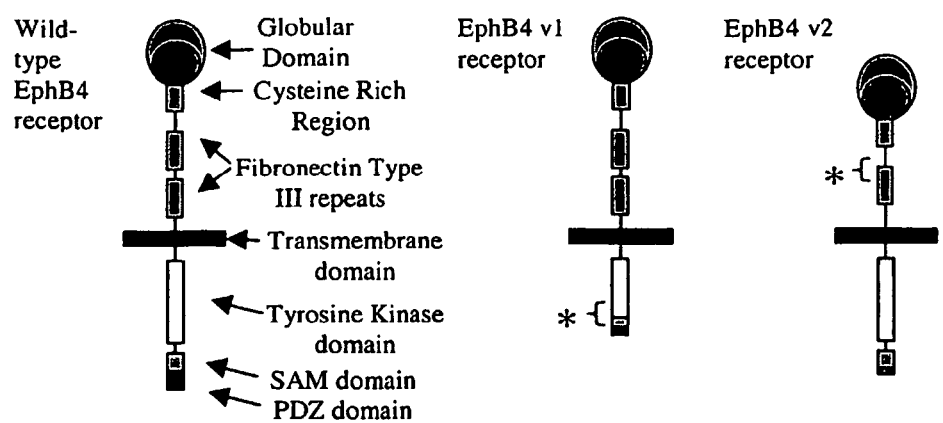
FIG. 9 shows a schematic diagram comparing the domains of the wild-type EphB4 receptor with the predicted structure of the slice variants EphB4v1 and EphB4v2. Deleted regions are indicated by *.

Several hybridising bands were obtained with Western blot analysis (data not shown). However, the identity of these protein bands that are specific to the tumour sample(s), and common to all tumour samples tested, remains to be determined but may correspond to splice variation. Two EphB4 splice variants (named EphB4v1 and EphB4v2) were identified. Determination of the EphB4 gene structure has shown that EphB4v1 results from the absence of the 53 amino acids encoded by the entire exon 16 (FIG. 9). If EphB4v1 is translated the resultant protein would lack a portion of both the kinase and SAM domains, two protein domains that are known to have roles in transmitting signals to intracellular targets. EphB4v2 is caused by the in-frame deletion of the entire exon 6 which results in the absence of 111 amino acids. EphB4v2 would encode a protein that lacks the first fibronectin type III repeat. The role of fibronectin type III repeats is not known and the effect of removing one of these repeats is unknown at this time.

EXAMPLE 5

RT-PCR Anlaysis of EphB4

Because of EphB4 possible role in angiogenesis, the expression of EphB4 in endothelial cells using RT-PCR was performed. Low level of expression of EphB4 was observed. However, when these cells were gown in the presence of the EphB4 polyclonal antibody (H-200-Santa Cruz Biotechnology) specifically directed to the extracellular domain amino residues 201 to 400 of EphB4 (SEQ ID NO:1) there was no apparent change in cell growth or morphology, even at the highest concentration of antibody. The effect of the EphB4 antibody on the growth and morphology of NIH3T3 cells was also tested. There was no morphological or growth response (data not shown). The nontumorigenic breast cell line MCF10A, established from mammary tissue from a 36-year old Caucasian patient with fibrocystic breast disease (21) was also tested and was observed to express EphB4 at low levels but did not respond to the anti-EphB4 antibody (data not shown). These results, when considered together with results gained from the western analysis of normal human tissues (Example 5), suggest that tissues that show a high level of EphB4 expression will be negatively affected by an EphB4 antibody.

Figure 10:
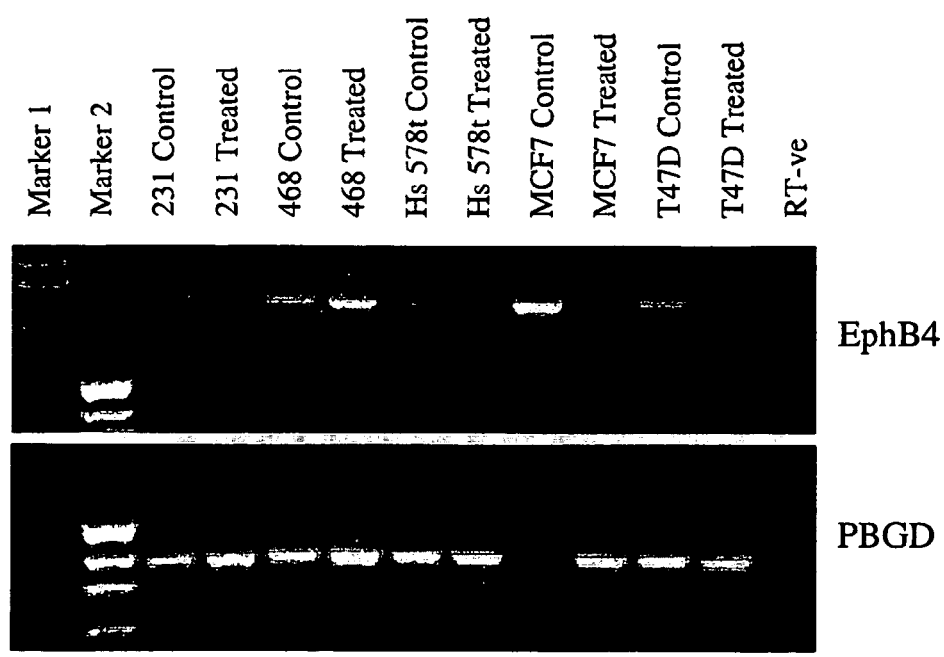
FIG. 10 shows an expression of EphB4gene and PBGD (housekeeping control) in breast cancer cell lines MDA-MB-231 (231), MDA-MB-468 (468), Hs578t, MCF7 and T47D either treated with 1/100 dilution of the EphB4 polyclonal antibody (H-200-Santa Cruz Biotechnology) specifically directed to the extracellular domain amino residues 201 to 400 of EphB4 (SEQ ID NO:1) for 65 h (Treated) or with no treatment (control). RT-ve is the reverse transcription reagents only control. Marker 1-Spp1/EcoR1 and Marker 2-pUC19/Hpa11.

The results indicated that after treatment with the EphB4 polyclonal antibody (H-200-Santa Cruz Biotechnology) specifically directed to the extracellular domain amino residues 201 to 400 of EphB4 (SEQ ID NO:1) the EphB4 gene is down-regulated (FIG. 10). This agrees with the finding that most antibodies increase RTK down-regulation and internalisation of the receptor after blocking the ligand-receptor interaction and inhibiting ligand-induced RTK signaling. This is since certain antibodies can influence tumour growth by altering the intracellular signaling pattern inside the targeted tumour cell. The analysis of global changes in gene expression in Ab-treated cells compared to untreated cells may identify genes involved in EphB4-related signaling.

EXAMPLE 6

EphB4 Antibody-Epitope Mapping

A EphB4 commercially available H-200 polyclonal Ab from Santa Cruz is raised against a recombinant protein corresponding to amino acids 201-400 of SEQ:ID:NO: 1 of EphB4 human receptor. The sequence includes the cysteine-rich domain and the first fibronectin type III repeat and accordingly it was expected that several different antigenic regions would be recognised. Six blocking peptides of 25 amino acids (overlap by 5 amino acids, offset by 20 amino acids) were designed against specific amino acid residues of EphB4 protein (SEQ ID NO.1) as indicated in FIG. 11. The blocking peptides have the following amino acid sequence:

```
Peptide 1   SEQ ID NO: 2:
TVNLTRFPETVPRELVVPVAGSCVV

Peptide 2   SEQ ID NO: 3:
GSCVVDAVPAPGPSPSLYCREDGQW
```

```
Peptide 3   SEQ ID NO: 4:
EDGQWAEQPVTGCSCAPGFEAAEGN

Peptide 4   SEQ ID NO: 5:
AAEGNTKCRACAQGTFKPLSGEGSC

Peptide 5   SEQ ID NO: 6:
GEGSCQPCPANSHSNTIGSAVCQCR

Peptide 6   SEQ ID NO: 7:
VCQCRVGYFRARTDPRGAPCTTPPS
```

Figure 12:
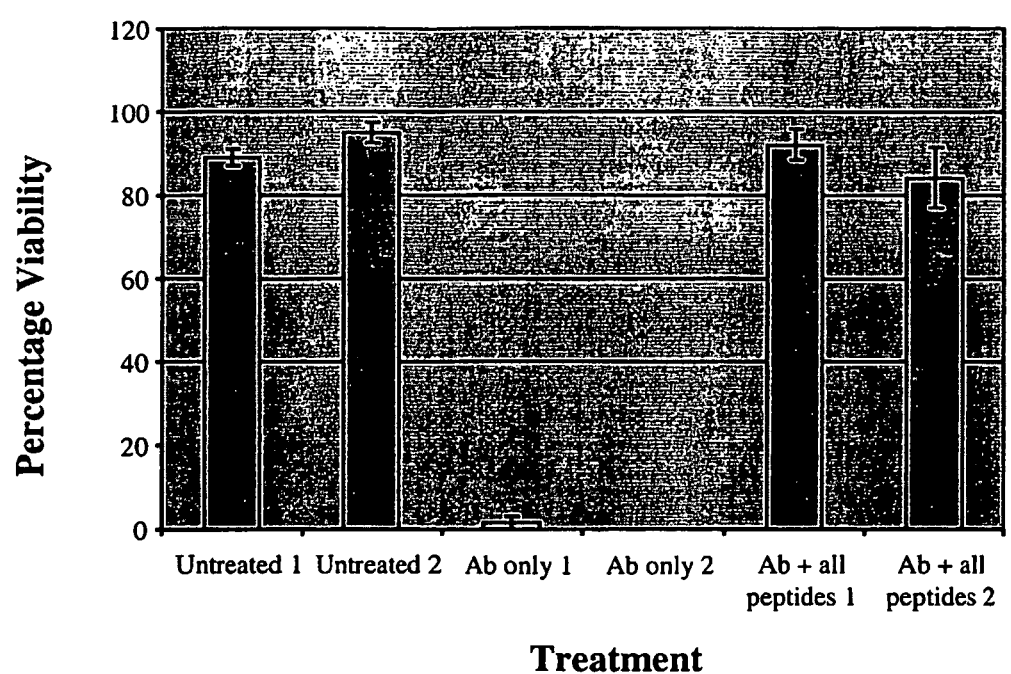
FIG. 12 shows a trypan blue exclusion assay comparing viability in control cells (untreated), cells with the EphB4 polyclonal antibody (H-200-Santa Cruz Biotechnology) specifically directed to the extracellular domain amino residues 201 to 400 of EphB4 (SEQ ID NO:1) alone (Ab only) or treated with both antibody and peptide cocktail (Ab+all peptides). Tests were performed in duplicate.
Figure 13:
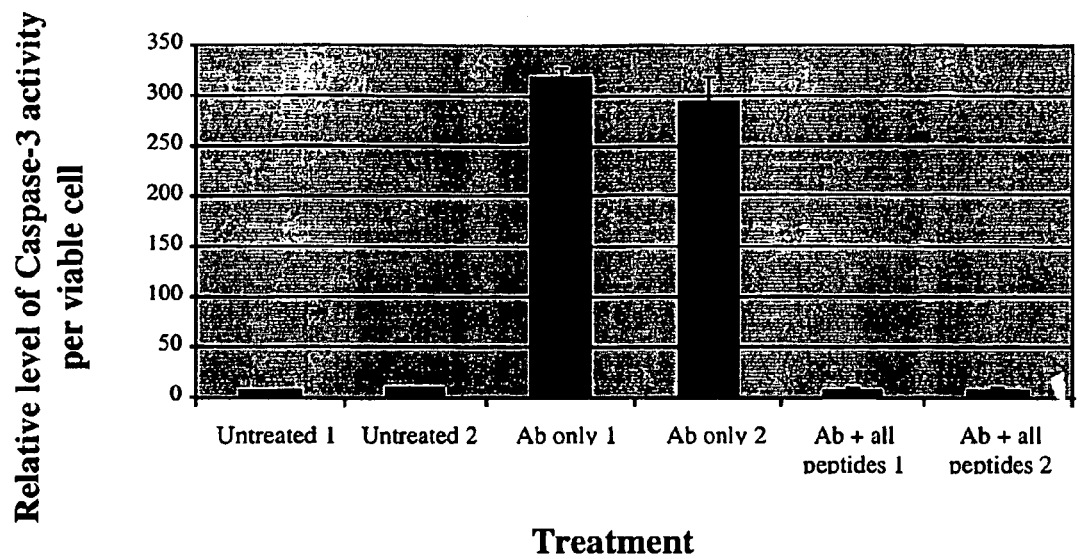
FIG. 13 shows an assay comparing relative levels of caspase-3 activity in control cells (untreated), cells with the EphB4 polyclonal antibody (H-200-Santa Cruz Biotechnology) specifically directed to the extracellular domain amino residues 201 to 400 of EphB4 (SEQ ID NO:1) alone, (Ab only) or treated with both antibody and peptide cocktail (Ab+all peptides). Tests were performed in duplicate.
Figure 14:
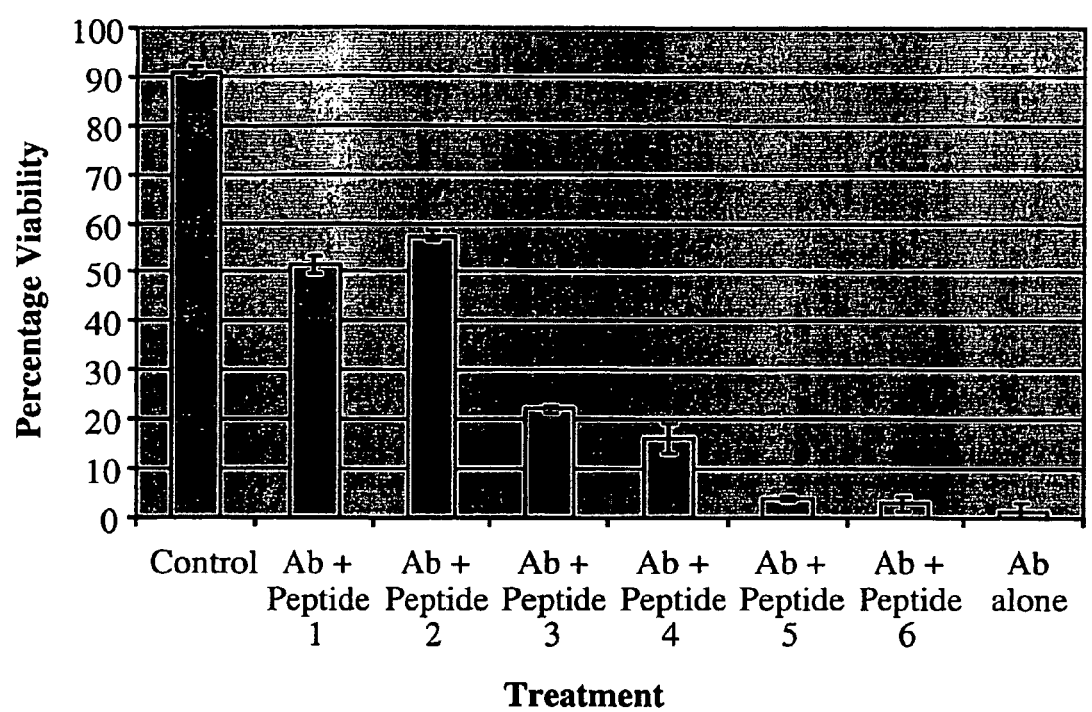
FIG. 14 shows results of trypan blue exclusion assay performed 48 h after treatment on confluent SW480 monolayers with a 1/500 dilution of the EphB4 polyclonal antibody (H-200-Santa Cruz Biotechnology) specifically directed to the extracellular domain amino residues 201 to 400 of EphB4 (SEQ ID NO:1) with or without 5 µl of peptides as indicated. Peptides 1 and 2 appeared to rescue ~50% of cells from Ab-mediated cell death.

The peptides were tested for their ability to prevent cell death after pre-incubation with the EphB4 polyclonal antibody (H-200-Santa Cruz Biotechnology) specifically directed to the extracellular domain amino residues 201 to 400 of EphB4 (SEQ ID NO:1). A cocktail of all the peptides was initially tested and successfully prevented cell death as determined using trypan blue exclusion (FIG. 12) and caspase-3 activity assays (FIG. 13). The peptides were then tested separately and partial rescue was observed for Peptide 1 (SEQ ID NO:2) and Peptide 2 (SEQ ID NO:3) (see FIG. 14). Peptide 1 and Peptide 2 overlap by five amino acids residues (GSCVV designated SEQ ID NO:13) indicating that this amino acid sequence corresponding to residues 221 to 225 of EphB4 (SEQ ID NO:1) is possibly the core of the reactive epitope.

Figure 15:
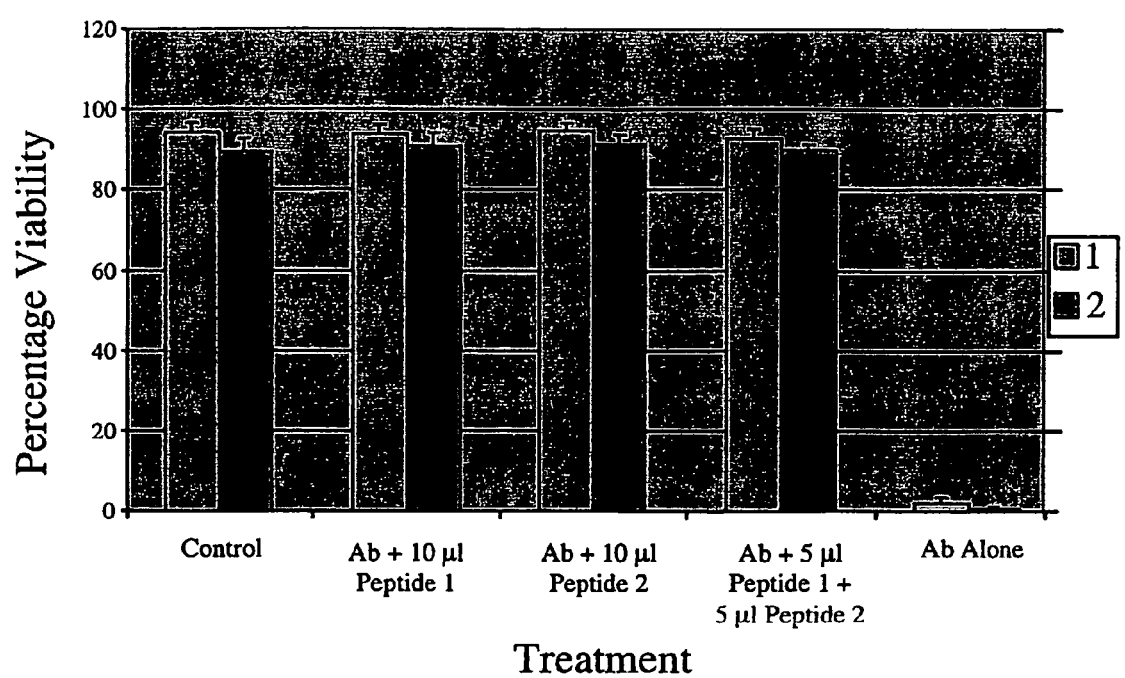
FIG. 15 shows an increase in the volume of Peptide 1 (SEQ ID NO:2) or Peptide 2 (SEQ ID NO:3) (to 10 µl) was able to fully rescue cells from the EphB4 polyclonal antibody (H-200-Santa Cruz Biotechnology) specifically directed to the extracellular domain amino residues 201 to 400 of EphB4 (SEQ ID NO:1) mediated cell death and was equal in effect to a combination of Peptides 1 and 2 (5 µl of each).

Because the initial experiment with the cocktail of peptides effectively contained twice the molar amount of the GSCVV (SEQ ID NO:13) sequence (ie residues 221 to 225 of EphB4 (SEQ ID NO:1)) a further blocking experiment in which twice the amount of each of Peptide 1 (SEQ ID NO:2) and Peptide 2 (SEQ ID NO:3) was compared with the initial amount of the peptides together. All treatments were successful in preventing tumour cell death caused by the EphB4 polyclonal antibody (H-200 from Santa Cruz) (see FIG. 15).

Three new peptides (Peptides 7 to 9) of different lengths that span the GSCVV (SEQ ID NO:13) core epitope sequence were made commercially based on specific amino acid residues of EphB4 protein (SEQ ID NO.1) as indicated in FIG. 16. The blocking peptides have the following amino acid sequence:

```
Peptide 7   SEQ ID NO: 8      AGSCVVDA

Peptide 8   SEQ ID NO: 9      VAGSCVVDAV

Peptide 9   SEQ ID NO: 10     LVVPVAGSCVVDAVPA.
```

Figure 17:
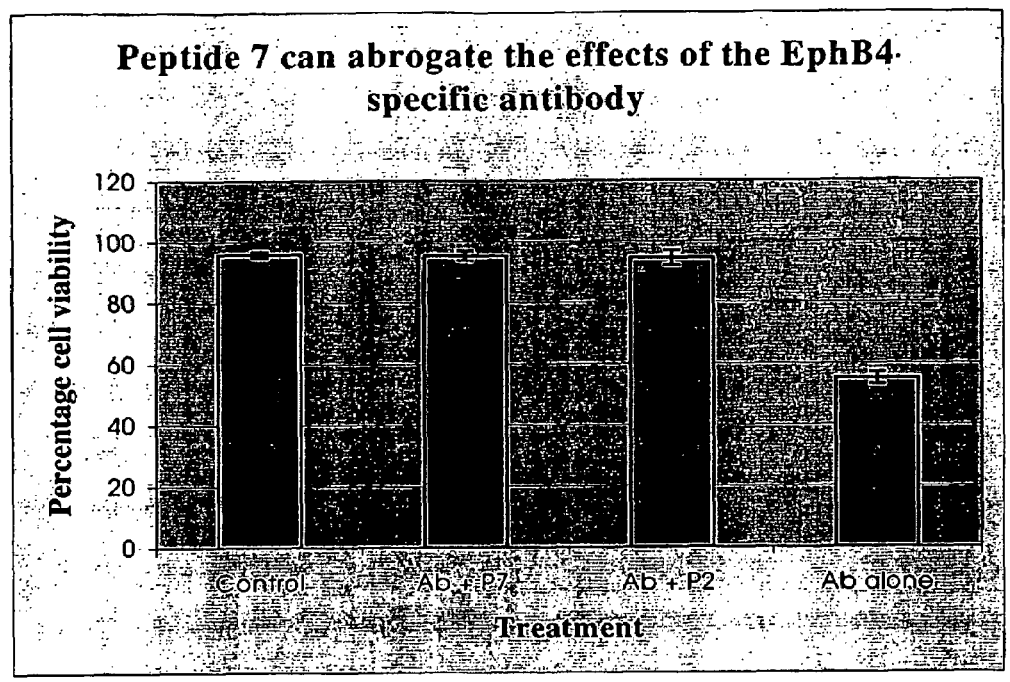
FIG. 17 shows Peptide 7 (SEQ ID NO: 8) was able to fully rescue cells from Ab-mediated cell death and was equal in effect to Peptide 2 (SEQ ID NO: 3). One microlitre of the EphB4 polyclonal antibody (H-200-Santa Cruz Biotechnology) specifically directed to the extracellular domain amino residues 201 to 400 of EphB4 (SEQ ID NO:1) (0.2 µg/ml) and 10 µl of a 10 mg/ml stock of peptide were pre-incubated together on ice for 2 h before addition to a confluent monolayer of cells in a 24-well microtitre plate with 500 µl of DMEM.
Figure 19:
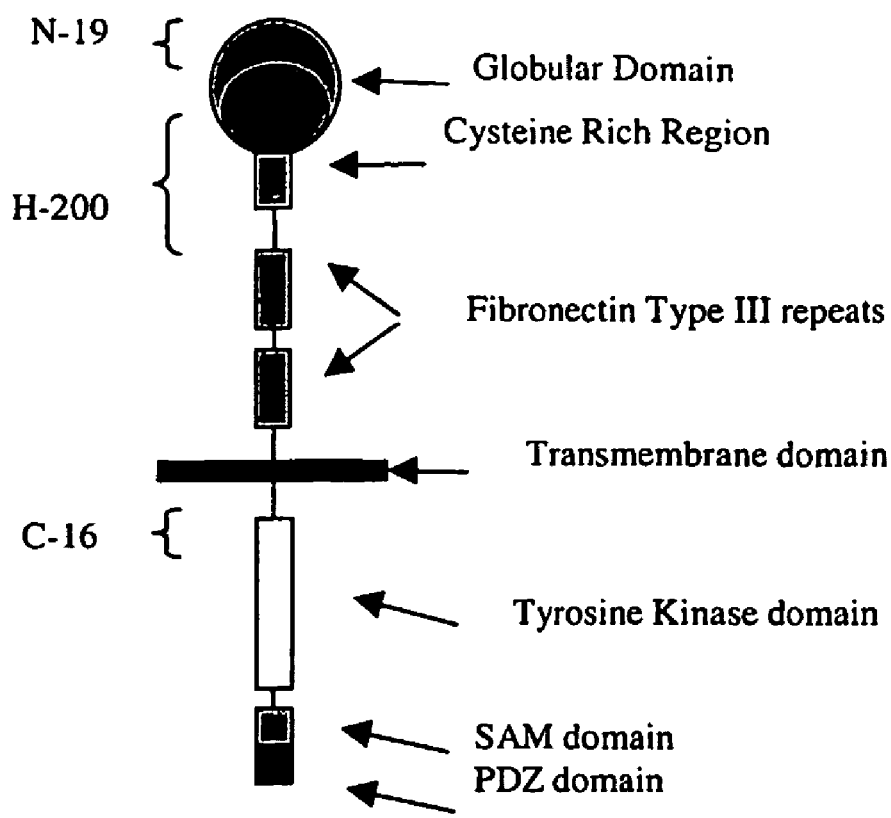
FIG. 19 shows a model of the EphB4 receptor with domain regions to which the different polyclonal antibodies (N-19, H-200 and C-16) have been targeted indicated by black brackets. The globular domain (ephrin receptor ligand binding domain) corresponds to residues 29 to 197 of EphB4 (SEQ ID NO:1). The cysteine-rich region (Giardia variant-specific surface protein) corresponds to residues 255 to 313 of EphB4 (SEQ ID NO:1). The fibronectin type III domain 1 corresponds to residues 324 to 414 of EphB4 (SEQ ID NO:1). The fibronectin type III domain corresponds to residues 437 to 517 of EphB4 (SEQ ID NO:1). The transmembrane domain corresponds to residues 540 to 560 of EphB4 (SEQ ID NO:1). The tyrosine kinase domain corresponds to residues 615 to 874 of EphB4 (SEQ ID NO:1). The SAM (sterile alpha motif) domain corresponds to residues 904 to 971 of EphB4 (SEQ ID NO:1). The PDZ domain corresponds to residues 985 to 987 of EphB4 (SEQ ID NO:1).

However, due to the high number of hydrophobic amino acids in peptides 8 and 9, these peptides were not soluble in any solution that could be applied to cells, thus preventing further testing. However, Peptide 7 (SEQ ID NO. 8) with an amino acid sequence corresponding to residues 220 to 227 of EphB4 (SEQ ID NO:1) was used in blocking experiments and was able to rescue cells from the cell death effect caused by the addition of the EphB4-antibody (H-200 from Santa Cruz) alone (see FIG. 17).

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or any other country before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Australian Institute of Health and Welfare (AIHW) and Australasian Association of Cancer Registries (AACR) 2000. Cancer in Australia 1997. AIHW cat no. CAN10. Canberra: AIHW (Cancer Series no. 15).
2. Wang et al., 1998, Cell 93:741-753.
3. Dottori et al., 1998, PNAS 1998 95:13248-13253.
4. Easty et al., 1999, Int. J. Cancer 84:494-501.
5. Tickle and Altabef, 1999, Curr. Opin. Genet. Dev. 9:455460.
6. Oates et al., 1999, Mech. Dev. 83:77-94.
7. O'Leary and Wilkinson, 1999, Curr. Opin. Neurobiol. 9:65-73.
8. Ward et al, 1989, Nature 341:544-546.
9. Van den Beuken T et al, 2001, J. Mol. Biol, 310, 591.
10. Bird et al, 1988, Science 242:423-426.
11. Huston et al., 1988 Proc. Natl. Acad. Sci. USA 85:5879-5883.
12. Holliger, P., et al 1993 Proc. Natl. Acad. Sci. USA 90:6444-6448.
13. Poljak, R. J., et al. 1994 Structure 2:1121-1123.
14. Kohler and Milstein (1975, Nature 256: 495-497.
15. Kozbor et al,. 1983, Immunology Today 4: 72.
16. Cole et al., 1985, in Monoclonal Antibodies and Cancer Therapy, Alan R. Liss, Inc., pp. 77-96.
17. Saraste and Pulkki, 2000, Cardiovascular Res. 45:528-53.
18. Tickle and Altabef (1999) Epithelial cell movements and interactions in limb, neural crest and vasculature. Curr. Opin. Genet. Dev. 9: 455-460
19. Mellitzer et al., 1999, Nature 400:77-81.
20. Bennett et al (1994) Cloning and characterization of HTK, a novel transmembrane tyrosine kinase of the EPH subfamily. J Biol. Chem. 269:14211-14218.
21. Keydar et al (1979) Establishment and characterization of a cell line of human breast carcinoma origin. Eur. J. Cancer 15:659-670.

The invention claimed is:

1. A method for inhibiting cancerous growth of a mammalian breast cancer cell that expresses EphB4, or a mammalian colon cancer cell that expresses EphB4, the method comprising contacting said cell with at least one antibody or an antigen-binding portion thereof, wherein said antibody or antigen-binding portion thereof binds an EphB4 epitope located within residues 200 to 400 of EphB4 (SEQ ID NO:1), binding said antibody or said antigen-binding portion thereof to said cell's EphB4, and inhibiting said cancerous growth as a result of said binding.

2. The method according to claim 1, wherein the antibody or antigen-binding portion thereof binds to an epitope located within residues 201 to 245 of EphB4 (SEQ ID NO:1).

3. The method according to claim 2, wherein the antibody or antigen-binding portion thereof binds to an epitope located within residues 220 to 244 of EphB4 (SEQ ID NO:1).

4. The method according to claim 3, wherein the antibody or antigen-binding portion thereof binds to an epitope located within residues 220 to 230 of EphB4 (SEQ ID NO:1).

5. The method of claim 1, wherein said cell is a human cell.

6. A method for inducing cell death of a mammalian breast cancer cell that expresses EphB4, or a mammalian colon cancer cell that expresses EphB4, the method comprising
contacting said cell with at least one antibody or an antigen-binding portion thereof, wherein the antibody or antigen-binding portion thereof binds an EphB4 epitope located within residues 200 to 400 of EphB4 (SEQ ID NO:1),
binding said antibody or said antigen-binding portion thereof to said cell's EphB4, and
inducing said cell death as a result of said binding.

7. The method according to claim 6, wherein the antibody or antigen-binding portion thereof binds to an epitope located within residues 201 to 245 of EphB4 (SEQ ID NO:1).

8. The method according to claim 7, wherein the antibody or antigen-binding portion thereof binds to an epitope located within residues 220 to 244 of EphB4 (SEQ ID NO:1).

9. The method according to claim 8, wherein the antibody or antigen-binding portion thereof binds to an epitope located within residues 220 to 230 of EphB4 (SEQ ID NO:1).

10. The method of claim 6, wherein said cell is a human cell.

11. A method for treating breast cancer or colon cancer in a mammalian subject, wherein said subject is in need of the inhibition of growth, or inducing the cell death of, of breast cancer cells, or colon cancer cells, that express EphB4,
the method comprising
administering to the subject an effective amount of at least one antibody or an antigen-binding portion thereof, wherein the antibody or antigen-binding portion thereof binds to an epitope located within residues 200 to 400 of EphB4 (SEQ ID NO:1),
contacting said antibody or said antigen-binding portion thereof with said cell as a result of said administering,
binding said antibody or said antigen binding portion thereof to said cell's EphB4 thereby inhibiting said growth of, or inducing the cell death of, said cancer cells, and
treating or preventing said cancer in said subject as a result of said binding.

12. The method according to claim 11, wherein the antibody or antigen-binding portion thereof binds to an epitope located within residues 201 to 245 of EphB4 (SEQ ID NO:1).

13. The method according to claim 12, wherein the antibody or antigen-binding portion thereof binds to an epitope located within residues 220 to 244 of EphB4 (SEQ ID NO:1).

14. The method according to claim 13, wherein the antibody or antigen-binding portion thereof binds to an epitope located within residues 220 to 230 of EphB4 (SEQ ID NO:1).

15. The method of claim 11, wherein said subject is human.

16. The method of any one of claims 1, 6 and 11, wherein the amino acid sequence of said cell's EphB4 comprises that of amino acids 200-400 of SEQ ID NO:1.

17. The method of any one of claims 1, 6 and 11, wherein said antibody is a monoclonal antibody.

* * * * *

```
                         SEQUENCE LISTING

<160> NUMBER OF SEQ ID NOS: 13

<210> SEQ ID NO 1
<211> LENGTH: 987
<212> TYPE: PRT
<213> ORGANISM: Homo sapiens

<400> SEQUENCE: 1

Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Asp Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190
```

-continued

```
Phe Tyr Lys Lys Cys Ala Gln Leu Thr Val Asn Leu Thr Arg Phe Pro
    195                 200                 205

Glu Thr Val Pro Arg Glu Leu Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
```

```
            610                 615                 620
Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
        675                 680                 685

Val Met Ile Leu Thr Glu Phe Met Glu Asn Gly Ala Leu Asp Ser Phe
690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
        755                 760                 765

Ser Ser Asp Pro Thr Tyr Thr Ser Ser Leu Gly Gly Lys Ile Pro Ile
770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
        835                 840                 845

Leu His Gln Leu Met Leu Asp Cys Trp Gln Lys Asp Arg Asn Ala Arg
850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Leu Val Ser Gln Ile Ser Ala
930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
            980                 985

<210> SEQ ID NO 2
<211> LENGTH: 25
<212> TYPE: PRT
<213> ORGANISM: Homo sapiens

<400> SEQUENCE: 2
```

```
Thr Val Asn Leu Thr Arg Phe Pro Glu Thr Val Pro Arg Glu Leu Val
1               5                   10                  15

Val Pro Val Ala Gly Ser Cys Val Val
            20                  25

<210> SEQ ID NO 3
<211> LENGTH: 25
<212> TYPE: PRT
<213> ORGANISM: Homo sapiens

<400> SEQUENCE: 3

Gly Ser Cys Val Val Asp Ala Val Pro Ala Pro Gly Pro Ser Pro Ser
1               5                   10                  15

Leu Tyr Cys Arg Glu Asp Gly Gln Trp
            20                  25

<210> SEQ ID NO 4
<211> LENGTH: 25
<212> TYPE: PRT
<213> ORGANISM: Homo sapiens

<400> SEQUENCE: 4

Glu Asp Gly Gln Trp Ala Glu Gln Pro Val Thr Gly Cys Ser Cys Ala
1               5                   10                  15

Pro Gly Phe Glu Ala Ala Glu Gly Asn
            20                  25

<210> SEQ ID NO 5
<211> LENGTH: 25
<212> TYPE: PRT
<213> ORGANISM: Homo sapiens

<400> SEQUENCE: 5

Ala Ala Glu Gly Asn Thr Lys Cys Arg Ala Cys Ala Gln Gly Thr Phe
1               5                   10                  15

Lys Pro Leu Ser Gly Glu Gly Ser Cys
            20                  25

<210> SEQ ID NO 6
<211> LENGTH: 25
<212> TYPE: PRT
<213> ORGANISM: Homo sapiens

<400> SEQUENCE: 6

Gly Glu Gly Ser Cys Gln Pro Cys Pro Ala Asn Ser His Ser Asn Thr
1               5                   10                  15

Ile Gly Ser Ala Val Cys Gln Cys Arg
            20                  25

<210> SEQ ID NO 7
<211> LENGTH: 25
<212> TYPE: PRT
<213> ORGANISM: Homo sapiens

<400> SEQUENCE: 7

Val Cys Gln Cys Arg Val Gly Tyr Phe Arg Ala Arg Thr Asp Pro Arg
1               5                   10                  15

Gly Ala Pro Cys Thr Thr Pro Pro Ser
            20                  25

<210> SEQ ID NO 8
<211> LENGTH: 8
```

-continued

```
<212> TYPE: PRT
<213> ORGANISM: Homo sapiens

<400> SEQUENCE: 8

Ala Gly Ser Cys Val Val Asp Ala
1               5

<210> SEQ ID NO 9
<211> LENGTH: 10
<212> TYPE: PRT
<213> ORGANISM: Homo sapiens

<400> SEQUENCE: 9

Val Ala Gly Ser Cys Val Val Asp Ala Val
1               5                   10

<210> SEQ ID NO 10
<211> LENGTH: 16
<212> TYPE: PRT
<213> ORGANISM: Homo sapiens

<400> SEQUENCE: 10

Leu Val Val Pro Val Ala Gly Ser Cys Val Val Asp Ala Val Pro Ala
1               5                   10                  15

<210> SEQ ID NO 11
<211> LENGTH: 25
<212> TYPE: PRT
<213> ORGANISM: Homo sapiens

<400> SEQUENCE: 11

Ala Gly Ser Cys Val Val Asn Ala Val Pro Ala Pro Gly Pro Ser Pro
1               5                   10                  15

Ser Leu Tyr Cys Arg Glu Asp Gly Gln
            20                  25

<210> SEQ ID NO 12
<211> LENGTH: 25
<212> TYPE: PRT
<213> ORGANISM: Homo sapiens

<400> SEQUENCE: 12

Ala Gly Ser Cys Val Val Asp Ala Val Pro Ala Pro Gly Pro Ser Pro
1               5                   10                  15

Ser Leu Tyr Cys Arg Glu Asp Gly Gln
            20                  25

<210> SEQ ID NO 13
<211> LENGTH: 5
<212> TYPE: PRT
<213> ORGANISM: Homo sapiens

<400> SEQUENCE: 13

Gly Ser Cys Val Val
1               5
```